US005084593A

United States Patent [19]

Gotoh et al.

[11] Patent Number: 5,084,593

[45] Date of Patent: Jan. 28, 1992

[54] LEUCO DYES AND RECORDING MATERIAL EMPLOYING THE SAME

[75] Inventors: Hiroshi Gotoh, Fuji; Shigeru Kusakata, Susono; Isao Shiojima, Mishima, all of Japan

[73] Assignee: Ricoh Company, Ltd., Tokyo, Japan

[21] Appl. No.: 627,583

[22] Filed: Dec. 14, 1990

Related U.S. Application Data

[62] Division of Ser. No. 367,684, Jun. 19, 1989, Pat. No. 5,008,238.

[30] Foreign Application Priority Data

| | | | |
|---|---|---|---|
| Jun. 20, 1988 | [JP] | Japan | 63-151964 |
| Sep. 6, 1988 | [JP] | Japan | 63-223780 |
| Sep. 16, 1988 | [JP] | Japan | 63-231785 |
| Sep. 21, 1988 | [JP] | Japan | 63-234836 |

[51] Int. Cl.[5] .......... C07C 255/34

[52] U.S. Cl. .......... 558/405; 427/151; 503/217; 503/218; 503/225; 558/406; 558/408; 558/409; 560/45; 560/47; 560/48; 564/92; 564/180; 564/185; 564/428; 564/442; 564/443

[58] Field of Search .......... 564/92, 180, 185, 428, 564/442, 443; 558/405, 406, 408, 409; 560/45, 47, 48

[56] References Cited

U.S. PATENT DOCUMENTS

| | | | |
|---|---|---|---|
| 3,957,288 | 5/1976 | Lemahieu et al. | 430/138 |
| 3,958,815 | 5/1976 | Poot et al. | 503/201 |
| 4,912,259 | 3/1990 | Kaneko et al. | 564/442 |

FOREIGN PATENT DOCUMENTS

| | | | |
|---|---|---|---|
| 1236279 | 9/1989 | Japan | 558/409 |
| 2080464 | 3/1990 | Japan | 564/92 |

OTHER PUBLICATIONS

Yoshiaki, U. et al., "New Leuco Dye for Recording Materials", CA 109, 119802x (1988).

Hideaki, F. et al., "Trivinylmethane Compounds for Color Formers for Recording Materials", CA, 108, 77360y (1988).

*Primary Examiner*—Glennon H. Hollrah

*Attorney, Agent, or Firm*—Oblon, Spivak, McClelland, Maier & Neustadt

[57] ABSTRACT

Leuco dyes of the formula (I) are disclosed,

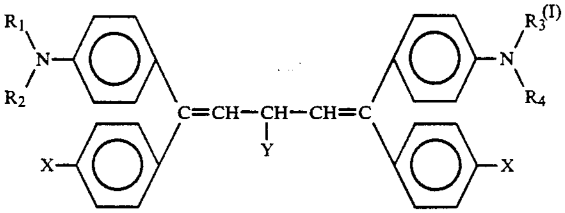

(I)

wherein $R_1$, $R_2$, $R_3$ and $R_4$ each represent an alkyl group having 1 to 10 carbon atoms; X represents hydrogen, an alkyl group having 1 to 10 carbon atoms, an alkoxy group having 1 to 10 carbon atoms or a halogen; and Y represents $R_5$—Z—$SO_2NH$—, $R_6$—Z—CONH—, or

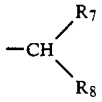

, in which Z represents

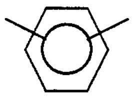

or

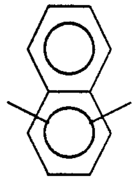

;

$R_5$ and $R_6$ each represent hydrogen, an alkyl group having 1 to 10 carbon atoms, or a halogen; and $R_7$ and $R_8$ each represent hydrogen, a cyano group, or —$COR_9$, in which $R_9$ represents a lower alkyl group, a lower alkoxyl group, a phenyl group which may be (Abstract continued on next page.)

substituted by an alkyl group having 1 to 4 carbon atoms, an alkoxyl group having 1 to 4 carbon atoms, or a halogen; a naphthyl group which may be substituted by an alkyl group having 1 to 4 carbon atoms, an alkoxyl group having 1 to 4 carbon atoms or a halogen with the proviso that $R_7$ and $R_8$ are not both hydrogen. Further a recording material comprising any of the above-mentioned leuco dyes and a particular phenolic compound as a color developer capable of inducing color formation in the leuco dye is disclosed.

9 Claims, 1 Drawing Sheet

FIG. I
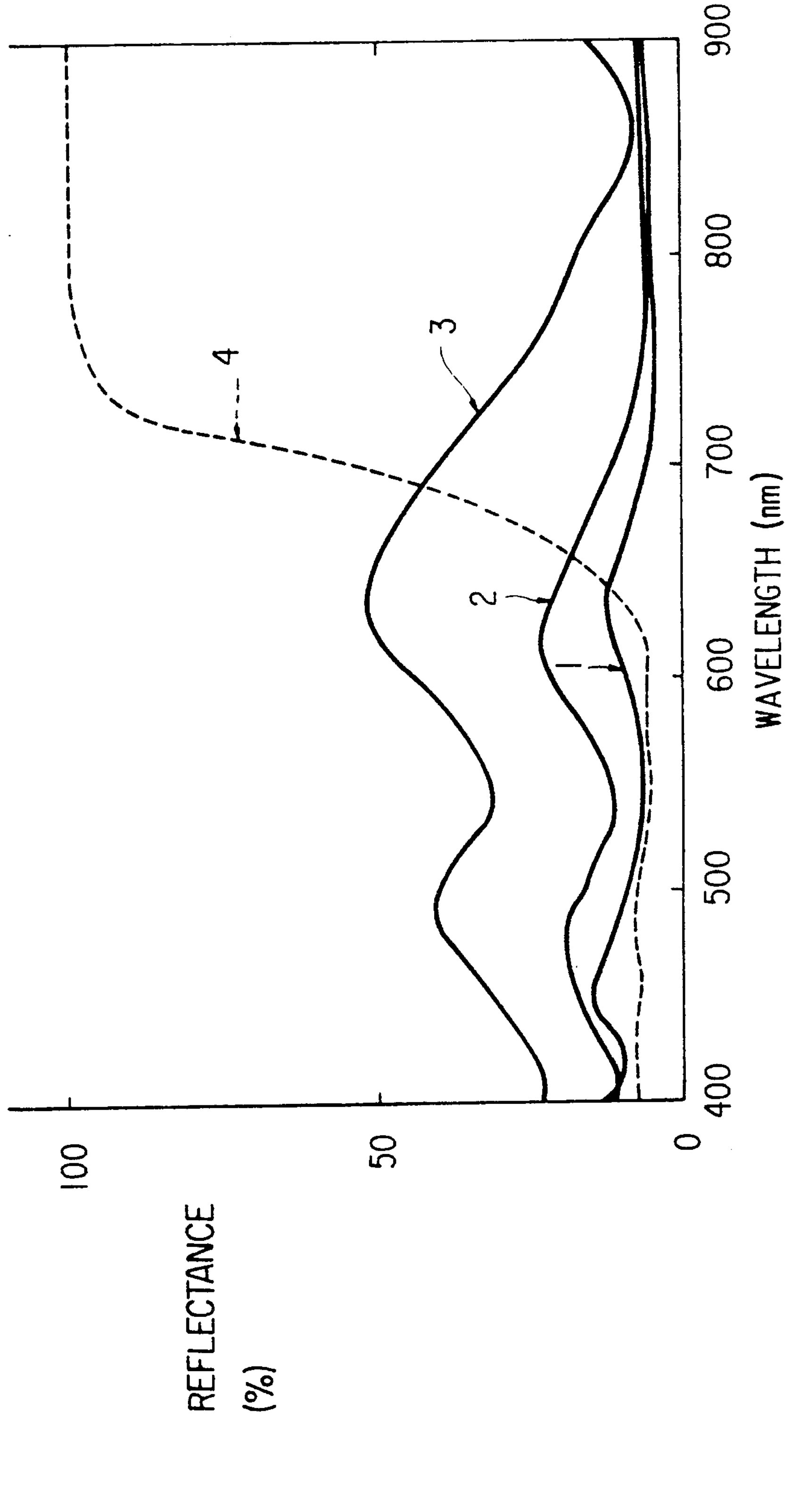

LEUCO DYES AND RECORDING MATERIAL EMPLOYING THE SAME

This is a division of application Ser. No. 07/367,684 filed on June 19, 1989 now U.S. Pat. No. 5,008,238.

BACKGROUND OF THE INVENTION

1. Field of the Invention

The present invention relates to leuco dyes having a sufficient absorption intensity in a near infrared region, which are capable of yielding colored images when brought into contact with an electron acceptor such as inorganic acids, organic acids, phenolic compounds and derivatives thereof, or oxidizing agents and a recording material using any of the above-mentioned leuco dyes as an electron donor coloring agent.

2. Discussion of Background

Recording materials using leuco dyes are conventionally known and used in practice, for example, as pressure-sensitive recording sheets and thermosensitive recording sheets. The consumption of the above-mentioned sheets shows a yearly increase.

The pressure-sensitive recording materials containing leuco dyes employ the reaction between a colorless or light-colored leuco dye and a color developer which is capable of inducing color formation in the leuco dye when brought into contact with the leuco dye. More specifically, the pressure-sensitive recording material comprises a coloring sheet and a color developer sheet. The coloring sheet is prepared by coating a microcapsuled organic solution of a leuco dye on a substrate, and the color developer sheet is prepared by coating mixture of the color developer and a binder agent on a substrate, separately. The pressure-sensitive recording material is constructed in such a manner that the above mentioned color developer sheet is overlaid on the coloring sheet, with the respective coated surfaces in contact with each other. When pressure is applied to the back side of the color developer sheet, for instance, by writing, the microcapsules of the leuco dye are ruptured to initiate the coloring reaction with the color developer.

Thermosensitive recording materials containing leuco dyes comprise a substrate and a thermosensitive coloring layer formed thereon comprising a leuco dye and a color developer. The thermosensitive recording material can yield colored images in response to thermal image signals applied from a heating resistor.

When the above-mentioned pressure-sensitive recording sheets and thermosensitive recording sheets are employed, recording can be more easily performed by using relatively simple apparatus without any complicated processes such as development and image fixing, in comparison with other recording materials such as electrophotographic recording materials and electrostatic recording materials. Therefore the pressure-sensitive recording sheets and thermosensitive recording sheets are utilized in various fields. Examples of-the leuco dyes contained in the conventional pressure-sensitive recording sheets and thermosensitive recording sheets include blue coloring dyes such as crystal violet lactone and leuco crystal violet, and black coloring dyes such as fluoran compounds substituted by an anilino group at the 7-position.

Recently optical character readers and label-bar code readers are developed and put into practice. These optical character readers and label bar-code readers generally employ, as a light source, a light emitting diode or a semiconductor laser having a wavelength of 700 nm or more. However, the above-mentioned conventional leuco dyes such as blue-coloring dyes and black-coloring dyes hardly show absorption intensity in a near infrared region of 700 nm or more, so that they cannot be used together with the above-mentioned optical character readers and bar-code readers Thus a demand for a novel leuco dye with a sufficient absorption intensity in a near infrared region of 700 nm or more is increasing.

Dyes and pigments showing sufficient absorption intensity in a near infrared region, such as phthalocyanine pigments, quinacridone pigments and chelate compounds of various metals, are conventionally known. These dyes and pigments, however, show high absorption intensity in the visible light range as well, so that they cannot be used for the pressure-sensitive recording materials and thermosensitive recording materials in an ordinary manner. To provide the above-mentioned dyes and pigments for the pressure-sensitive and thermosensitive recording materials, the dyes and pigments must be turned into the form of a leuco compound which is ordinarily colorless or light-colored, but is capable of yielding colored images when brought into contact with an electron acceptor.

There are conventionally proposed several leuco dyes having a sufficient absorption intensity in a near infrared region, for example, divinyl-containing phthalide compounds as disclosed in Japanese Laid-Open Patent Applications 51-121035, 51-121037, 51-121038, 51-167979, 58-157779 and 61-165380; spirofluorenephthalide compounds as disclosed in Japanese Laid-Open Patent Applications 59-199757, 60-226871, 61-22076 and 62-104872; and fluoran compounds as disclosed in Japanese Laid-Open Patent Applications 57-169484 and 62-196177.

However, the above-mentioned conventional leuco dyes have their own shortcomings. For example, the divinyl-containing phthalide compounds are intensely colored in yellow in their original state, and the manufacturing cost thereof is high due to the difficulty in synthesizing them. The spirofluorenephthalide compounds and fluoran compounds have also the shortcomings that their absorption intensity in a near infrared region is weaker than in the visible light range.

SUMMARY OF THE INVENTION

It is therefore an object of the present invention to provide novel leuco dyes for use in a recording material.

A second object of the present invention is to provide a recording material using any of the above leuco dyes, capable of yielding colored images which sufficiently absorb light in a near infrared region.

A third object of the present invention is to provide thermosensitive recording materials using any of the above leuco dyes, capable of yielding colored images which sufficiently absorb light in a near infrared region and have excellent color inducing performance and preservability.

A fourth object of the present invention is to provide a dye-containing composition.

According to the present invention, the first object of the present invention can be attained by leuco dyes having the following formula (I), which colored when brought into contact with a color developer capable of inducing color formation in the leuco dye:

(I)

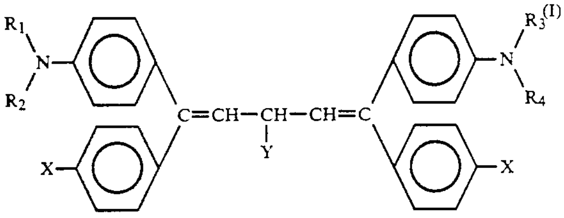

wherein $R_1$, $R_2$, $R_3$ and $R_4$ each represent an alkyl group having 1 to 10 carbon atoms; X represents hydrogen, an alkyl group having 1 to 10 carbon atoms, an alkoxyl group having 1 to 10 carbon atoms or a halogen; and Y represents $R_5$—Z—$SO_2NH$, $R_6$—Z—CONH, or

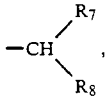, in which Z represents

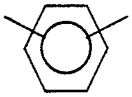 or 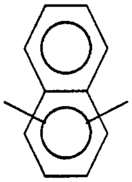;

$R_5$ and $R_6$ each represent hydrogen, an alkyl group having 1 to 10 carbon atoms, or a halogen; and $R_7$ and $R_8$ each represent hydrogen, provided that both $R_7$ and $R_8$ may not be hydrogen, a cyano group, or —$COR_9$, in which $R_9$ represents a lower alkyl group, a lower alkoxyl group, a phenyl group which may be substituted by an alkyl group having 1 to 4 carbon atoms, an alkoxyl group having 1 to 4 carbon atoms, or a halogen; a naphthyl group which may be substituted by an alkyl group having 1 to 4 carbon atoms, an alkoxyl group having 1 to 4 carbon atoms or a halogen.

The second object of the present invention can be attained by a recording material comprising at least one of the above-mentioned leuco dyes having the formula (I), which is colored when brought into contact with a color developer capable of inducing color formation in the leuco dye.

The third object of the present invention can be attained by a thermosensitive recording material comprising a substrate and a-thermosensitive coloring layer formed thereon, which thermosensitive coloring layer comprises at least one of the above-mentioned leuco dyes having the formula (I), serving as an electron-donating color inducing agent, and at least one of phenolic compounds having the formulas (VI), (VII) and (VIII), serving as an electron acceptor.

(VI)

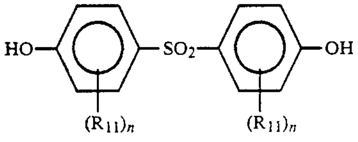

wherein $R_{11}$ represents an alkyl group having 1 to 6 carbon atoms, a halogen, or an aryl group; and n is an integer of 0 to 2.

(VII)

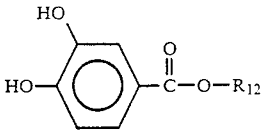

wherein $R_{12}$ represents an alkyl group having 1 to 18 carbon atoms, an aryl group or an aralkyl group.

(VIII)

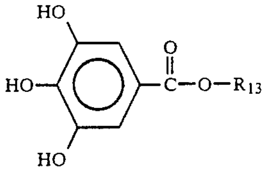

wherein $R_{13}$ represents an alkyl group having 12 to 22 carbon atoms or an aralkyl group.

The fourth object of the present invention can be attained by a dye-containing composition comprising at least one leuco dye of the formula (I) and at least one electron acceptor-color developer selected from the phenolic compounds having the above-mentioned formulas (VI), (VII) and (VIII), which is capable of inducing a coloring reaction when in contact with the leuco dye of the formula (I).

BRIEF DESCRIPTION OF THE DRAWINGS

A more complete appreciation of the invention and many of the attendant advantages thereof will be readily obtained as the same becomes better understood by reference to the following detailed description when considered in connection with the accompanying single drawing, wherein:

The single figure shows the reflectivity of each colored image area of thermosensitive recording materials No. 1, No. 2 and No. 3 according to the present invention, and the reflectivity of a colored image area of a comparative thermosensitive recording material.

DETAILED DESCRIPTION OF THE PREFERRED EMBODIMENTS (I)

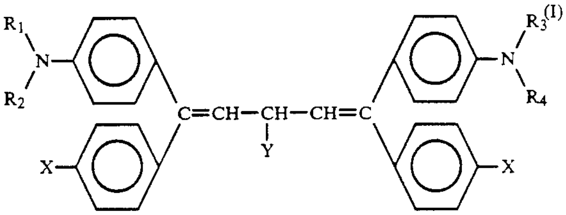

In the above formula (I) of the leuco dye according to the present invention, preferable examples of the alkyl group represented by $R_1$, $R_2$, $R_3$, $R_4$, $R_5$, $R_6$ or X are a methyl group, an ethyl group, a propyl group, a n-butyl group, an isobutyl group, a pentyl group, a hexyl group and a heptyl group. Preferable examples of the alkoxyl group represented by X are a methoxy group, an ethoxy group, a propoxy group, an n-butoxy group, an isobutoxy group and a pentoxy group. Examples of the halogen represented by X, $R_5$ and $R_6$ are chlorine, bromine and fluorine.

The leuco dyes having the formula (I) according to the present invention, which are colorless or lightly colored solids, stable in air, are readily colored when brought into molecular-level contact with electron accepting compounds, for example, inorganic acids such as activated clay and acid clay, organic acids, phenolic compounds and derivatives thereof, and oxidizers. The leuco dyes according to the present invention are then allowed to induce dark purple color, which results in the formation of clear colored images. The above-mentioned colored dye shows excellent preservability, so that the leuco dyes are useful as a precursor of the purple dyes. The $\lambda_{max}$ of the light absorption spectrum of the dyes is in the range of about 800 to 850 nm in a solvent. The light absorption spectrum of the dyes when colored on a sheet of paper is in the range of about 400 to 950 nm. The colored image area on the recording material according to the present invention is excellent from the viewpoints of heat resistance, humidity resistance and water resistance.

When the leuco dye according to the present invention is employed alone, the obtained colored image area can form a contrast to an area not colored on the recording material.

In the present invention, the color tone of the colored image area on the recording material can be controlled by using the leuco dyes according to the present invention in combination.

Examples of the leuco dyes having the formula (I) according to the present invention are given as follows, but are not intended to be limiting thereof.

1,1,5,5-tetrakis(p-dimethylaminophenyl)-3-hydroxy-1,4-pentadiene,
1,1,5,5-tetrakis(p-diethylaminophenyl)-3-hydroxy-1,4-pentadiene,
1,1-bis-(p-dimethylaminophenyl)-5,5-bis-(p-diethylaminophenyl)-3-hydroxy-1,4-pentadiene,
1,1,5,5-tetrakis(p-dimethylaminophenyl)-3-p-toluenesulfinyl-1,4-pentadiene,
1,1,5,5-tetrakis(p-dimethylaminophenyl)-3-benzenesulfinyl-1,4-pentadiene,
1,1,5,5-tetrakis(p-dimethylaminophenyl)-3-p-chlorobenzenesulfinyl-1,4-pentadiene,
1,1,5,5-tetrakis(p-dimethylaminophenyl)-3-α-naphthalenesulfinyl-1,4-pentadiene,
1,1,5,5-tetrakis(p-dimethylaminophenyl)-3-β-naphthalenesulfinyl-1,4-pentadiene,
1,1,5,5-tetrakis(p-diethylaminophenyl)-3-p-toluenesulfinyl-1,4-pentadiene,
1,1,5,5-tetrakis(p-diethylaminophenyl)-3-benzenesulfinyl-1,4-pentadiene,
1,1-bis(p-dimethylaminophenyl)-5,5-bis(p-diethylaminophenyl)-3-p-toluenesulfinyl-1,4-pentadiene,
1,1,5,5-tetrakis(p-dimethylaminophenyl)-1,4-pentadiene-3-p-toluenesulfonamide,
1,1,5,5-tetrakis(p-dimethylaminophenyl)-1,4-pentadiene-3-o-toluenesulfonamide,
1,1,5,5-tetrakis(p-dimethylaminophenyl)-1,4-pentadiene-3-benzenesulfonamide,
1,1,5,5-tetrakis(p-diethylaminophenyl)-1,4-pentadiene-3-p-toluenesulfonamide,
1,1,5,5-tetrakis(p-diethylaminophenyl)-1,4-pentadiene-3-o-toluenesulfonamide,
1,1,5,5-tetrakis(p-diethylaminophenyl)-1,4-pentadiene-3-benzenesulfonamide,
1,1,5,5-tetrakis(p-dimethylaminophenyl) -1,4-pentadiene-3-p-chlorobenzenesulfonamide,
1,1,5,5-tetrakis(p-dimethylaminophenyl)-1,4-pentadiene-3-o-aminobenzenesulfonamide,
1,1,5,5-tetrakis(p-dimethylaminophenyl)-1,4-pentadiene-3-p-aminobenzenesulfonamide,
1,1,5,5-tetrakis(p-dimethylaminophenyl)-1,4-pentadiene-3-p-dimethylaminobenzenesulfonamide,
1,1,5,5-tetrakis(p-dimethylaminophenyl)-1,4-pentadiene-3-α-naphthalenesulfonamide,
1,1,5,5-tetrakis(p-dimethylaminophenyl)-1,4-pentadiene-3-β-naphthalenesulfonamide,
1,1,5,5-tetrakis(p-diethylaminopheynl)-1,4-pentadiene-3-α-naphthalenesulfonamide,
1,1,5,5-tetrakis(p-diethylaminophenyl)-1,4-pentadiene-3-β-naphthalenesulfonamide,
1,1,5,5-tetrakis(p-dimethylaminophenyl)-1,4-pentadiene-3-benzamide,
1,1,5,5-tetrakis(p-diethylaminophenyl)-1,4-pentadiene-3-benzamide,
1,1,5,5-tetrakis(p-dimethylaminophenyl)-1,4-pentadiene-3-p-methylbenzamide,
1,1,5,5-tetrakis(p-diethylaminophenyl)-1,4-pentadiene-3-p-methylbenzamide,
1,1,5,5-tetrakis(p-dimethylaminophenyl)-1,4-pentadiene-3-p-chlorobenzamide,
1,1,5,5-tetrakis(p-diethylaminophenyl)-1,4-pentadiene-3-p-chlorobenzamide,
1,1,5,5-tetrakis(p-dimethylaminophenyl)-1,4-pentadiene-3-p-trifluoromethylbenzamide,
1,1,5,5-tetrakis(p-diethylaminophenyl)-1,4-pentadiene-3-p-trifluoromethylbenzamide,
1,1,5,5-tetrakis(p-dimethylaminophenyl)-1,4-pentadiene-3-p-hyiroxybenzamide,
1,1,5,5-tetrakis(p-dimethylaminophenyl)-1,4-pentadiene-3-p-aminobenzamide,
1,1,5,5-tetrakis(p-dimethylaminophenyl)-1,4-pentadiene-3-p-nitrobenzamide,
1,1,5,5-tetrakis(p-dimethylaminophenyl)-1,4-pentadiene-3-p-dimethylaminobenzamide,
1,1,5,5-tetrakis(p-dimethylaminophenyl)-1,4-pentadiene-3-o-methylbenzamide,
1,1,5,5-tetrakis(p-dimethylaminophenyl)-1,4-pentadiene-3-o-chlorobenzamide,
1,1,5,5-tetrakis(p-dimethylaminophenyl)-1,4-pentadiene-3-p-amidobenzamide,
1,1,5,5-tetrakis(p-dimethylaminophenyl)-1,4-pentadiene-3-α-naphthoamide,
1,1,5,5-tetrakis(p-dimethylaminophenyl)-1,4-pentadiene-3-β-naphthoamide,
1,1,5,5-tetrakis(p-diethylaminophenyl)-1,4-pentadiene-3-α-naphthoamide,
1,1,5,5-tetrakis(p-diethylaminophenyl)-1,4-pentadiene-3-β-naphthoamide,
1,5-bis(p-dimethylaminophenyl)-1,5-bis(p-methoxyphenyl)-1,4-pentadiene-3-p-toluenesulfonamide (Leuco Dye No. 1 in Table 1),
1,5-bis(p-diethylaminophenyl)-1,5-bis(p-chlorophenyl)-1,4-pentadiene-3-p-toluenesulfonamide, (Leuco Dye No. 2 in Table 1),
1,5-bis(p-dimethylaminophenyl)-1,5-diphenyl-1,4-pentadiene-3-benzenesulfonamide, (Leuco Dye No. 3 in Table 1),
1,5-bis(p-dimethylaminophenyl)-1,5-bis(p-methoxyphenyl)-1,4-pentadiene-3-α-naphthalenesulfonamide (Leuco Dye No. 4 in Table 1), 1,5-bis(p-dimethylaminophenyl)-1,5-bis(p-methoxy-phenyl)-1,4-pentadiene-3-$\beta$-naphthalenesulfonamide (Leuco Dye No. 5 in Table 1), 1,5-bis(p-dimethylaminophenyl)-1,5-bis(p-chloro-phenyl)-1,4-pentadiene-3-pchlorobenzenesulfonamide, (Leuco Dye No. 6 in Table 1), 1,5-bis(p-dimethylaminophenyl)-1,5-bis(p-methoxy-phenyl)-1,4-pentadiene-3-p-methylbenzamide, (Leuco Dye No. 7 in Table 1), 1,5-bis(p-dimethylaminophenyl)-1,5-diphenyl-1,4-pentadiene-3-p-methylbenzamide (Leuco Dye No. 8 in Table 1), 1,5-bis(p-dimethylaminophenvl)-1,5-bis(p-chloro-phenyl)-1,4-pentadiene-3-p-methylbenzamide (Leuco Dye No. 9 in Table 1), 1,5-bis(p-dimethylaminophenyl)-1,5-bis(p-chloro-phenyl)-1,4-pentadiene-3-benzamide 1,5-bis(p-diethylaminophenyl)-1,5-bis(p-chlorophenyl)-1,4-pentadiene-3-benzamide (Leuco Dye No. 10 in Table 1)

1,5-bis(p-dimethylaminophenyl)-1,5-bis(pmethyl-phenyl)-1,4-pentadiene-3-p-methylbenzamide, (Leuco Dye No. 11 in Table 1), 1,5-bis(p-diethylaminophenyl)-1,5-bis(p-chlorophenyl)-1,4-pentadiene-3-p-methylbenzamide (Leuco Dye No. 12 in Table 1), 1,5-bis(p-dimethylaminophenyl)-1,5-bis(pmethoxy-phenyl)-1,4-pentadiene-3-$\alpha$-naphthoamide (Leuco Dye No. 13 in Table 1), 1,5-bis(p-dimethylaminophenyl)-1,5-bis(p-methoxy-phenyl)-1,4-pentadiene-3-$\beta$-naphthoamide (Leuco Dye No. 14 in Table 1), 1,1,5,5-tetrakis(p-dimethylaminophenyl)-1,4-pentadiene-3-malonitrile, 1,1,5,5-tetrakis(p-dimethylaminophenyl)-1,4-pentadiene-3-acetophenone, 1,1,5,5-tetrakis(p-dimethylaminophenyl)-1,4-pentadiene-3-$\beta$-acetylnaphthalene, 1,1,5,5-tetrakis(p-dimethylaminophenyl)-1,4-pentadiene-3-acetylacetone, 1,1,5,5-tetrakis(p-dimethylaminophenyl)-1,4-pentadiene-3-benzoylmethane, 1,1,5,5-tetrakis(p-dimethylaminophenyl)-1,4-pentadiene-3-dimethyl malonate, 1,1,5,5-tetrakis(p-diethylaminophenyl)-1,4-pentadiene-3-dimethyl malonate, 1,1,5,5-tetrakis(p-dimethylaminophenyl)-1,4-pentadiene-3-diethyl malonate, 1,1,5,5-tetrakis(p-dimethylaminophenyl)-1,4-pentadiene-3-di-n-butyl malonate, 1,5-bis(p-dimethylaminophenyl)-1,5-bis(pmethyl-phenyl)-1,4-pentadiene-3-dimethyl malonate (Leuco Dye No. 15 in Table 1), 1,5-bis(p-dimethylaminophenyl)-1,5-bis(p-methoxy-phenyl)-1,4-pentadiene-3-dimethyl malonate (Leuco Dye No. 16 in Table 1), 1,5-bis(p-dimethylaminophenyl)-1,5-diphenyl-1,4-pentadiene-3-dimethyl malonate (Leuco Dye No. 17 in Table 1), 1,5-bis(p-dimethylaminophenyl)-1,5-bis(p-chloro-phenyl)-1,4-pentadiene-3-dimethyl malonate (Leuco Dye No. 18 in Table 1), 1,5-bis(p-dimethylaminophenyl)-1,5-bis(p-methoxy-phenyl)-1,4-pentadiene-3-malonitrile (Leuco Dye No. 19 in Table 1), 1,5-bis(p-dimethylaminophenyl)-1,5-bis(pmethoxy-phenyl)-1,4-pentadiene-3-acetylacetone, (Leuco Dye No. 20 in Table 1), 1,5-bis(p-diethylaminophenyl)-1,5-bis(p-methoxy-phenyl)-1,4-pentadiene-3-dimethyl malonate (Leuco Dye No. 21 in Table 1), 1,5-bis(p-diethylaminophenyl)-1,5-bis(p-methylphenyl)-1,4-pentadiene-3-dimethyl malonate 1,5-bis(p-dimethylaminophenyl)-1,5-diphenyl-1,4-pentadiene-3-diethyl malonate (Leuco Dye No. 22 in Table 1), 1,5-bis(p-dimethylaminophenyl)-1,5-bis(pmethoxy-phenyl)-1,4-pentadiene-3-diethyl malonate (Leuco Dye No. 23 in Table 1), 1,5-bis(p-dimethylaminophenyl)-1,5-bis(p-methoxy-phenyl)-1,4-pentadiene-3-di-n-butyl malonate (Leuco Dye No. 24 in Table 1), 1,5-bis(p-dimethylaminophenyl)-1,5-bis(p-methyl-phenyl)-1,4-pentadiene-3-diethyl malonate, 1,5-bis(p-dimethylaminophenyl)-1,5-bis(p-chloro-phenyl)-1,4-pentadiene-3-di-n-butyl malonate (Leuco Dye No. 25 in Table 1), 1,5-bis(p-dimethylaminophenyl)-1,5-bis(p-methyl-phenyl)-1,4-pentadiene-3-di-n-butyl malonate, 1,5-bis(p-di-n-butylaminophenyl)-1,5-bis(p-methoxy-phenyl)-1,4-pentadiene-3-acetylacetone (Leuco Dyc No. 26 in Table 1)

1,5-brs(p-di-n-butylaminophenyl)-1,5-bis(p-methyl-phenyl)-1,4-pentadiene-3-acetylacetone (Leuco Dye No. 27 in Table 1)

1,5-bis(p-di-n-butylaminophenyl)-1,5-bis(p-methoxy-phenyl)-1,4-pentadiene-3-dimethyl malonate (Leuco Dye No. 28 in Table 1), and 1,5-bis(p-di-n-butylaminophenyl)-1,5-bis(p-methyl-phenyl)-1,4-pentadiene-3-dimethyl malonate.

Some of the above-mentioned leuco dyes according to the present invention are described in detail in Table 1.

TABLE 1

| Leuco Dye Na | Substituents in Formula (I) $R_1, R_2, R_3, R_4$ | X | Y | Induced Color in Contact with Silica Gel |
|---|---|---|---|---|
| 1 | $-CH_3$ | $-OCH_3$ | 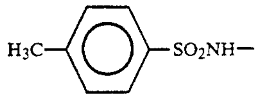 | intense purple |
| 2 | $-C_2H_5$ | $-Cl$ | 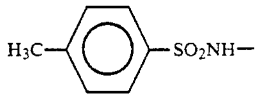 | dark purple |

TABLE 1-continued

| Leuco Dye Na | Substituents in Formula (I) $R_1$, $R_2$, $R_3$, $R_4$ | X | Y | Induced Color in Contact with Silica Gel |
|---|---|---|---|---|
| 3 | $-CH_3$ | $-H$ | 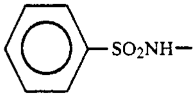 | blue-purple |
| 4 | $-CH_3$ | $-OCH_3$ | 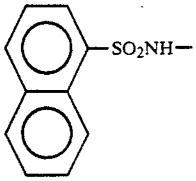 | intense purple |
| 5 | $-CH_3$ | $-OCH_3$ | 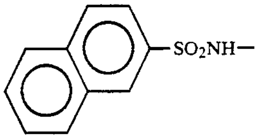 | intense purple |
| 6 | $-CH_3$ | $-Cl$ | 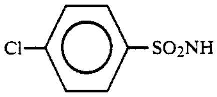 | dark purple |
| 7 | $-CH_3$ | $-OCH_3$ | 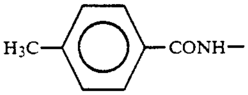 | intense purple |
| 8 | $-CH_3$ | $-H$ | 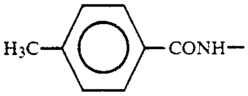 | blue-purple |
| 9 | $-CH_3$ | $-Cl$ | 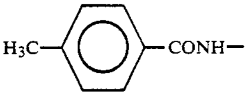 | dark purple |
| 10 | $-C_2H_5$ | $-Cl$ | 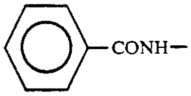 | dark purple |
| 11 | $-CH_3$ | $-CH_3$ | 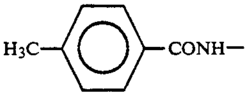 | dull blue-purple |
| 12 | $-C_2H_5$ | $-Cl$ | 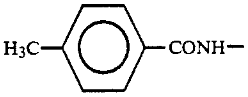 | dark purple |
| 13 | $-CH_3$ | $-OCH_3$ | 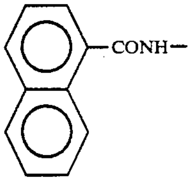 | intense purple |

TABLE 1-continued
| Leuco Dye Na | Substituents in Formula (I) R1, R2, R3, R4 | X | Y | Induced Color in Contact with Silica Gel |
|---|---|---|---|---|
| 14 | $-CH_3$ | $-OCH_3$ | 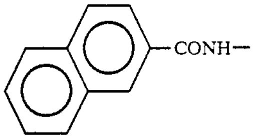 | intense purple |
| 15 | $-CH_3$ | $-CH_3$ | 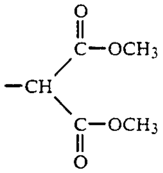 | dull blue-purple |
| 16 | $-CH_3$ | $-OCH_3$ | 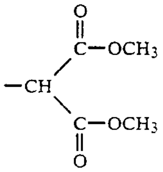 | intense purple |
| 17 | $-CH_3$ | $-H$ | 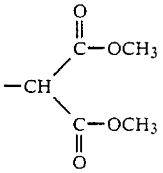 | blue-purple |
| 18 | $-CH_3$ | $-Cl$ | 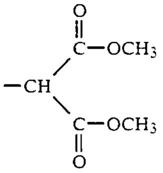 | dark purple |
| 19 | $-CH_3$ | $-OCH_3$ | 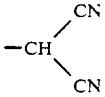 | intense purple |
| 20 | $-CH_3$ | $-OCH_3$ | 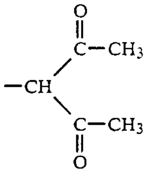 | intense purple |
| 21 | $-C_2H_5$ | $-OCH_3$ | 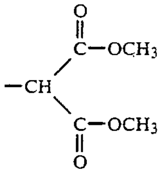 | intense purple |
| 22 | $-CH_3$ | $-H$ | 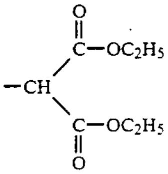 | blue-purple |

TABLE 1-continued

| Leuco Dye Na | Substituents in Formula (I) | | | Induced Color in Contact with Silica Gel |
|---|---|---|---|---|
| | $R_1$, $R_2$, $R_3$, $R_4$ | X | Y | |
| 23 | $-CH_3$ | $-OCH_3$ | 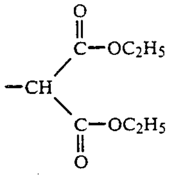 | intense purple |
| 24 | $-CH_3$ | $-OCH_3$ | 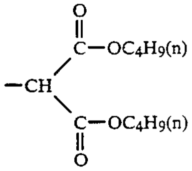 | intense purple |
| 25 | $-CH_3$ | $-Cl$ | 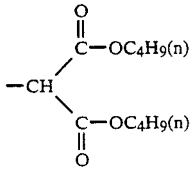 | dark purple |
| 26 | -n-$C_4H_9$ | $-OCH_3$ | 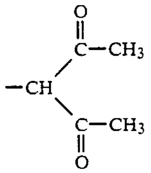 | intense purple |
| 27 | -n-$C_4H_9$ | $-CH_3$ | 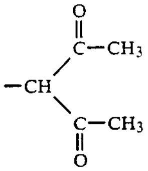 | dull blue-purple |
| 28 | -n-$C_4H_9$ | $-OCH_3$ | 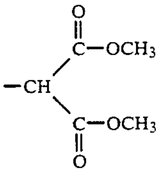 | intense purple |

The leuco dyes having the formula (I) according to the present invention can be synthesized as follows:

A derivative of 1,5-bis-(p-dialkylaminophenyl)-1,5-bis-(phenyl)-2,4-pentadiene-1-al-perchlorate of the formula (II) is caused to react with any of the compounds of formulas (III), (IV) and (V) in an organic solvent at a temperature ranging from 0° C. to 80° C. The obtained product is purified by the use of an organic solvent, whereby a leuco dye of the formula (I) can be obtained in the form of white or lightly colored crystals.

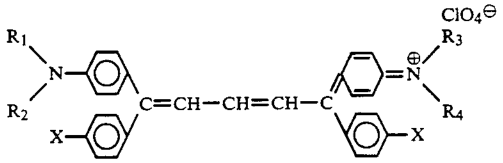

(II)

wherein $R_1$, $R_2$, $R_3$ and $R_4$ each represent a lower alkyl group; and X represents hydrogen, a lower alkyl group, a lower alkoxyl group, or a halogen.

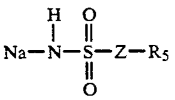

(III)

-continued

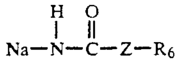

(IV)

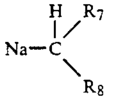

(V)

wherein Z represents

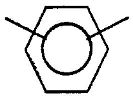

or

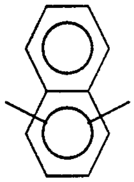

;

$R_5$ and $R_6$ each represent hydrogen, a lower alkyl group or a halogen; $R_7$ and $R_8$ each represent hydrogen, a cyano group or —$COR_9$ in which $R_9$ represents an alkyl group, an alkoxyl group, a substituted or unsubstituted phenyl group, and a substituted or unsubstituted naphthyl group provided that $R_7$ and $R_8$ are not both hydrogen.

A synthesis example of the above-mentioned 1,5-bis(p-dialkylaminophenyl)-1,5-bis(phenyl)-2,4-pentadiene-1-alperchlorate derivative of the formula (II) is described in Journal of the American Chemical Society, Vol. 80, page 3772 (1958).

The leuco dyes according to the present invention can be used as a coloring agent for use in pressure-sensitive recording materials, thermosensitive recording materials and thermal image transfer recording materials as other conventional leuco dyes. A pressure-sensitive recording material by use of the leuco dyes according to the present invention can be obtained by the manner as described in U.S. Pat. No. 2,800,457, and a thermosensitive recording material by use of the leuco dyes according to the present invention can be obtained by the manner as described in Japanese Laid-Open Patent Application 45-14039.

In the present invention, the leuco dyes of the formula (I) according to the present invention may be used together with other conventional leuco dyes when necessary. In this case, any conventional leuco dyes for use in conventional thermosensitive materials can be employed. For example, triphenylmethane-type leuco compounds, fluoran-type leuco compounds, phenothiazine-type leuco compounds, auramine-type leuco compounds, spiropyran-type leuco compounds and indolinophthalide-type leuco compounds are preferably employed.

Specific examples of those leuco dyes are as follows:

3,3-bis(p-dimethylaminophenyl)-phthalide,
3,3-bis(p-dimethylaminophenyl)-6-dimethylaminophthalide (or Crystal Violet Lactone),
3,3-bis(p-dimethylaminophenyl)-6-diethylaminophthalide,
3,3-bis(p-dimethylaminophenyl)-6-chlorophthalide,
3,3-bis(p-dibutylaminophenyl)-phthalide,
3-cyclohexylamino-6-chlorofluoran,
3-dimethylamino-5,7-dimethylfluoran,
3-N-methyl-N-isobutyl-6-methyl-7-anilinofluoran,
3-N-ethyl-N-isoamyl-6-methyl-7-anilinofluoran,
3-diethylamino-7-chlorofluoran, 3-diethylamino-7-methylfluoran,
3-diethylamino-7,8-benzfluoran,
3-diethylamino-6-methyl-7-chlorofluoran,
3-(N-p-tolyl-N-ethylamino)-6-methyl-7-anilinofluoran,
3-pyrrolidino-6-methyl-7-anilinofluoran,
2-[N-(3′-trifluoromethylphenyl)amino]-6-diethylaminofluoan,
2-[3,6-bis(diethylamino)-9-(o-chloroanilino)xanthylbenzoic acid lactam],
3-diethylamino-6-methyl-7-(m-trichloromethylanilino)-fluoran,
3-diethylamino 7-(o-chloroanilino)fluoran,
3-dibutylamino-7-(o-chloroanilino)fluoran,
3-N-methyl-N-amylamino-6-methyl-7-anilinofluoran,
3-N-methyl-N-cyclohexylamino-6-methyl-7-anilinofluoran,
3-diethylamino-6-methyl-7-anilinofluoran,
3-diethylamino-6-methyl-7-(2′,4′-dimethylanilino)fluoran,
3-(N,N-diethylamino)-5-methyl-7-(N,N-dibenzylamino) fluoran,
Benzoyl leuco methylene blue,
6′-chloro-8′-methoxy-benzoindolino-spiropyran,
6′-bromo-3′-methoxy-benzoindolino-spiropyran,
3-(2′-hydroxy-4′-dimethylaminophenyl)-3-(2′-methoxy-5′-chlorophenyl)phthalide,
3-(2′-hydroxy-4′-dimethylaminophenyl)-3-(2′-methoxy-5′-nitrophenyl)phthalide,
3-(2′-hydroxy-4′-diethylaminophenyl)-3-(2′-methoxy-5′-methylphenyl)phthalide,
3-(2′-methoxy-4′-dimethylaminophenyl)-3-(2′-hydroxy-4′-chloro-5′-methylphenyl)phthalide,
3-morpholino-7-(N-propyl-trifluoromethylanilino)fluoran,
3-pyrrolidino-7-trifluoromethylanilinofluoran,
3-diethylamino-5-chloro-7-(N-benzyl-trifluoromethylanilino)fluoran,
3-pyrrolidino-7-(di-p-chlorophenyl)methylaminofluoran,
3-diethylamino-5-chloro-7-(α-phenylethylamino)fluoran,
3-(N-ethyl-p-toluidino)-7-(α-phenylethylamino)fluoran,
3-diethylamino-7-(o-methoxycarbonylphenylamino)-fluoran,
3-diethylamino-5-methyl-7-(α-phenylethylamino)fluoran,
3-diethylamino-7-piperidinofluoran,
2-chloro-3-(N-methyltoluidino)-7-(p-n-butylanilino)-fluoran,
3-(N-methyl-N-isopropyl)amino-6-methyl-7-anilinofluoran,
3-dibutylamino-6-methyl-7-anilinofluoran,
3,6-bis(dimethylamino)fluorenespiro(9,3′)-6′-dimethylaminophthalide,
3-(N-benzyl-N-cyclohexylamino)-5,6-benzo-7-α-naphthylamino-4′-bromofluoran,
3-diethylamino-6-chloro-7-anilinofluoran,
4-(N-ethyl-N-ethoxypropyl)amino-6-methyl-7-anilinofluoran,
3-(N-ethyl-N-tetrahyirofurfuryl)amino-6-methyl-7-anilinofluoran, and
3-diethylamino-6-methyl-7-mesidino-4′,5′-benzofluoran.

As the color developers for use in combination with the above leuco dyes in the present invention, a variety of electron acceptors capable of inducing color formation in the leuco dyes when coming into contact with the leuco dyes can be employed.

Specific examples of such color developers are phenolic compounds, thiophenolic compounds, thiourea derivatives, and organic acids and metallic salts thereof, for example:

4,4'-isopropylidenebisphenol,
4,4'-isopropylidenebis(o-methylphenol),
4,4'-sec-butylidenebisphenol,
4,4'-isopropylidenebis(2-tert-butylphenol),
4,4'-cyclohexylidenediphenol,
4,4'-isopropylidenebis(2-chlorophenol),
2,2'-methylenebis(4-methyl-6-tert-butylphenol),
2,2'-methylenebis(4-ethyl-6-tert-butylphenol),
1,1,3-tris(2-methyl-4-hydroxy-5-tertbutylphenyl)butane,
1,1,3-tris(2-methyl-4-hydroxy-5-cyclohexylphenyl)butane,
4,4'-thiobis(6-tert-butyl-2-methylphenol),
4,4'-diphenolsulfone,
4-isopropoxy-4'-hydroxydiphenylsulfone,
4-benzyloxy-4'-hydroxydiphenylsulfone,
4,4'-diphenolsulfoxide,
isopropyl p-hydroxybenzoate,
benzyl p-hydroxybenzoate,
benzyl protocatechuate,
stearyl gallate,
lauryl gallate,
octyl gallate,
1,7-bis(4-hydroxyphenylthio)-3,5-dioxaheptane,
1,5-bis(4-hydroxyphenylthio)-3-oxapentane,
1,3-bis(4-hydroxyphenylthio)-propane,
1,3-bis(4-hydroxyphenylthio)-2-hydroxypropane,
N,N'-diphenylthiourea,
N,N'-di(m-chlorophenyl)thiourea,
salicylanilide,
5-chloro-salicylanilide,
2-hydroxy-3-naphthoic acid,
2-hydroxy-1-naphthoic acid,
1-hydroxy-2-naphthoic acid,
zinc hydroxynaphthoic acid,
aluminum hydroxynaphthoic acid,
calcium hydroxynaphthoic acid,
bis(4-hydroxyphenyl)methyl acetate,
bis(4-hydroxyphenyl)benzyl acetate,
1,3-bis(4-hydroxycumyl)benzene,
1,4-bis(4-hydroxycumyl)benzene,
2,4'-diphenolsulfone,
3,3'-diallyl-4,4'-diphenolsulfone,
3,4-dihydroxy-4'-methyldiphenylsulfone,
$\alpha,\alpha$-bis(4-hydroxyphenyl)-$\alpha$-methyltoluene,
antipyrine complex of zinc thiocyanate,
tetrabromobisphenol A, and
tetrabromobisphenol S.

According to the present invention, in particular, when the thermosensitive recording material is prepared by using the above-mentioned leuco dyes having the formula (I) and any of the specific phenolic compounds having the formulas (VI), (VII) and (VIII) serving as a color developer, the thus prepared thermosensitive recording material can show excellent color inducing performance and colored image preservability.

Specific examples of the above phenolic compounds having the formula (VI) are as follows:

bis(4-hydroxyphenyl)sulfone,
bis(3-aryl-4-hydroxyphenyl)sulfone,
bis(3-methyl-4-hydroxyphenyl)sulfone,
bis(3-butyl-4-hydroxyphenyl)sulfone,
bis(3,5-diaryl-4-hydroxyphenyl)sulfone,
bis(3-chloro-4-hydroxyphenyl)sulfone,
3-aryl-4,4'-dihydroxydiphenylsulfone,
bis(2-ethyl-4-hydroxyphenyl)sulfone,
3-isopropyl-4,4'-dihydroxydiphenylsulfone,
bis(2,5-dimethyl-4-hydroxyphenyl)sulfone, and
bis(2,5-dichloro-4-hydroxyphenyl)sulfone.

Specific examples of the above phenolic compounds having the formula (VII) are as follows:

methyl-3,4-dihydroxybenzoate,
ethyl-3,4-dihydroxybenzoate,
n-propyl-3,4-dihydroxybenzoate,
n-butyl-3,4-dihydroxybenzoate,
n-octyl-3,4-dihydroxybenzoate,
n-dodecyl-3,4-dihydroxybenzoate,
n-hexadecyl-3,4-dihydroxybenzoate,
n-octadecyl-3,4-dihydroxybenzoate,
phenyl-3,4-dihydroxybenzoate,
naphthyl-3,4-dihydroxybenzoate,
benzyl-3,4-dihydroxybenzoate,
2'-methylbenzyl-3,4-dihydroxybenzoate,
4'-methylbenzyl-3,4-dihydroxybenzoate,
2'-chlorobenzyl-3,4-dihydroxybenzoate,
4'-chlorobenzyl-3,4-dihydroxybenzoate,
$\alpha$-naphthylmethyl-3,4-dihydroxybenzoate, and
2'-methyl-$\alpha$-naphthylmethyl-3,4-dihydroxybenzoate.

Specific examples of the above phenolic compounds having the formula (VIII) are as follows:

n-dodecyl gallate,
n-hexadecyl gallate,
n-octadecyl gallate,
n-docosyl gallate,
benzyl gallate,
4'-methylbenzyl gallate,
4'-chlorobenzyl gallate,
2',4'-dichlorobenzyl gallate,
2'-chlorobenzyl gallate,
phenethyl gallate,
$\alpha$-naphthylmethyl gallate, and
2'-methyl-$\alpha$-naphthylmethyl gallate.

In the case where the thermosensitive recording material comprises the above-mentioned leuco dye and phenolic compound, it is preferable that the amount of the phenolic compound contained in the thermosensitive coloring layer of the thermosensitive recording material be 0.1 to 6 parts by weight to 1 part by weight of the leuco dye.

A pressure-sensitive recording material by use of the leuco dyes according to the present invention can be prepared, for example as follows:

The above leuco dye is prepared in the form of a microcapsule by the conventional methods, for instance, by a method as described in U.S. Pat. No. 2,800,457. More specifically, diisopropyl naphthalene type oil or terphenyl type oil in which the leuco dye is dissolved at a concentration of 1 to 4% is contained in a shell of a microcapsule made of a cured resin such as gelatin, which microcapsule has a particle diameter of about 5 $\mu$m. The thus obtained microcapsules comprising the leuco dyes therein are coated on a sheet of paper or a plastic film by means of an appropriate binder agent, whereby a coloring sheet is obtained. On the other hand, a color developer sheet is obtained as follows: The above-mentioned color developer is dispersed in water or an organic solvent by means of an appropriate dispersant. To the thus prepared dispersion, an appropriate binder agent is added when necessary, and this dispersion is coated on a substrate such as a sheet of paper. The coated surface of the color developer sheet is attached to the coated surface of the coloring sheet, so that a pressure-sensitive recording material can be obtained when pressure is applied to the non-coated surface of the color developer sheet of the pressure-sensitive recording material, for instance, by writing, the microcapsules containing the leuco dyes of the coloring sheet are destroyed and the leuco dyes are brought into contact with the color developer in the color developer sheet, which induces color formation in the color developer sheet.

A thermosensitive recording material by use of the leuco dyes according to the present invention can be prepared, for example as follows:

The leuco dye, the color developer, and auxiliary components of a filler such as calcium carbonate and a thermofusible material such as stearic acid amide, which are separately dispersed in an aqueous dispersion, are mixed with addition of an appropriate binder agent. The thus prepared mixture is coated on a substrate such as a sheet of paper, nonwoven fabric, plastic film, synthetic paper, metallic foil, or a composite thereof, and then dried. In such a case, it is preferable that the volume mean diameter of the leuco dye be in the range of 1 to 4 μm, when the prevention of preferably in the range of 1 to 4 μm, when the prevention of fogging on the background of the recording material and the prevention of decrease in the thermosensitivity of the recording material are taken into consideration. When thermal energy is supplied to the thermosensitive recording material by a thermal head, the leuco dye and the color developer are fused and brought into contact with each other, thereby yielding colored images.

According to the present invention, a thermal image transfer recording material can be prepared by laminating two substrates which comprise the leuco dye and the color developer, respectively. Specifically, the leuco dye is dispersed or dissolved in water or a solvent. This dispersion is coated on a conventionally employed heat-resistant substrate such as a polyester film to form an image transfer sheet, while an image receiving sheet can be prepared by dispersing or dissolving the color developer in water or a solvent, and then coating this dispersion or solution on the other substrate. When the surface of the image transfer sheet is heated, colored images are obtained on the image receiving sheet.

In order to obtain a thermosensitive recording material according to the present invention, a variety of conventional binder agents can be employed for binding the above-mentioned leuco dyes and color developers to a substrate of the thermosensitive recording material. Further, in order to obtain a pressure-sensitive recording material according to the present invention, the same binder agents can also be employed for fixing the leuco dyes in the form of microcapsules and the color developers to the substrate of the pressure-sensitive recording material.

Specific examples of the above binder agents are polyvinyl alcohol; starch, starch derivatives; cellulose derivatives such as methoxycellulose, hydroxyethylcellulose, carboxymethylcellulose, methylcellulose, and ethylcellulose; other water-soluble polymers such as sodium polyacrylate, polyvinyl pyrrolidone, acrylamide - acrylic acid ester copolymer, acrylamide - acrylic acid ester - methacrylic acid terpolymer, alkali salts of styrene - maleic anhydride copolymer, alkali salts of isobutylene - maleic anhydride copolymer, polyacrylamide, sodium alginate, gelatin and casein; emulsions such as polyvinyl acetate, polyurethane, polyacrylic acid acid ester, polymethacrylic acid ester, vinyl chloride - vinyl acetate copolymer, ethylene - vinyl acetate copolymer; and latex such as styrene - butadiene copolymer and styrene - butadiene - acrylic copolymer.

As previously mentioned, auxiliary additive components which are used in the conventional thermosensitive and pressure-sensitive recording materials, such as fillers, surface active agents, thermofusible materials (or lubricants), dispersants, induced colored image stabilizers, antioxidants, photo-stabilizers, and fluorescent whitening agents may be employed together with the above-mentioned leuco dyes and color developers.

Examples of the filler for use in the present invention are finely-divided inorganic powders of calcium carbonate, silica, zinc oxide, titanium oxide, aluminum hydroxide, zinc hydroxide, barium sulfate, clay, talc, surface-treated calcium, and surface-treated silica, and finely-divided organic powders of urea - formaldehyde resin, styrene-methacrylic acid copolymer, and polystyrene resin.

Examples of the thermofusible materials are aliphatic acids such as stearic acid and behenic acid, aliphatic acid amides such as stearic acid amide palmitic acid amide, metallic salts of aliphatic acid such as zinc stearate, aluminum stearate, calcium stearate, zinc palmitate and zinc behenate, p-benzylbiphenyl, terphenyl, triphenylmethane, benzyl p-benzyloxy benzoate, β-benzyoxynaphthalene, β-phenyl ester naphthoate, 1-hydroxy-2-phenyl ester naphthoate, 1-hydroxy-2-methyl ester naphthoate, diphenyl carbonate, dibenzyl ester terephthalate, dimethyl ester terephthalate, 1,4-dimethoxy naphthalene, 1,4-diethoxy naphthalene, 1,4-dibenzyloxy naphthalene, 1,2-bis(phenoxy)ethane, 1,2-bis(3-methylphenoxy)ethane, 1,2-bis(4-methylphenoxy)ethane, 1,4-bis(phenoxy)butane, 1,4-bis(phenoxy)-2-butene, dibenzoylmethane, 1,4-bis(phenylthio)butane, 1,4-bis(phenylthio)-2-butene, 1,3-bis(2-vinyloxyethoxy)benzene, 1,4-bis(2-vinyloxyethoxy)benzene, p-(2-vinyloxyethoxy)-biphenyl, p-allyloxy biphenyl, p-propergyloxy biphenyl, dibenzoyloxymethane, 1,3-dibenzoyloxypropane, dibenzyl disulfide, 1,1-diphenylethanol, 1,1-diphenylpropanol, p-(benzyloxy)benzyl alcohol, 1,3-diphenoxy-2-propanol, N-octadecylcarbamoyl-p-methoxycarbonylbenzene, and N-octadecylcarbamoyl benzene.

The recording materials according to the present invention can be employed in various fields just like conventional ones. In particular, since the leuco dyes contained in the recording material according to the present invention have the advantage of a sufficient absorption intensity in a near infrared region, such recording materials can be utilized for an optical character reader, label bar-code reader and bar-code reader.

When the recording material according to the present invention is used as a thermosensitive recording adhesive label sheet, a thermosensitive coloring layer comprising the above leuco dye and the color developer is formed on the front side of the substrate, and an adhesive layer is formed on the back side cf the substrate, with a disposable backing sheet attached to the adhesive layer. In such a case, a protective layer can be formed on the surface of the thermosensitive coloring layer for the purpose of improving the image stability, when necessary. The main components of the protective layer are various water-soluble resins, latex, photo-setting resins. Fillers, water-resistance property improving agents, water repellants, anti-foaming agents and ultraviolet light absorbers may be added when necessary.

Other features of this invention will become apparent in the course of the following description of exemplary embodiments, which are given for illustration of the invention and are not intended to be limiting thereof

SYNTHESIS EXAMPLE 1-1

[Synthesis of α-(p-dimethylaminophenyl)-α-(p-methylphenyl)ethylene]

In a stream of nitrogen, 4.2 g of magnesium and 50 ml of absolute diethyl ether were placed in a 1-liter four-necked flask and stirred. To this mixture, a mixed solution of 25 g of methyl iodide and 50 ml of absolute diethyl ether was slowly added dropwise at room temperature over a period of 90 minutes. After the addition of the mixed solution, the reaction mixture was refluxed for 1 hour, so that a Grignard agent was prepared.

To the Grignard agent placed in the four-necked flask, 500 ml of a benzene solution of 20.7 g of 4-N,N-dimethylamino-4'-methylbenzophenone was added dropwise over a period of 90 minutes, with the temperature kept at 15 to 20° C. under ice cooling. After the dropwise addition of the benzene solution of 4-N,N-dimethylamino-4'-methylbenzophenone, the reaction mixture was refluxed for 1 hour and then allowed to stand overnight.

This reaction mixture was slowly added to 500 ml of the ice-cooled aqueous solution containing 40.6 g of glacial acetic acid and 77.3 g of ammonium chloride. The mixture was stirred at room temperature for 2 hours and then allowed to stand for a while.

The reaction mixture separated into a benzene layer in which a reaction product was contained and a water layer. The benzene layer was separated from this reaction mixture, and the water layer was extracted with benzene to obtain the reaction product contained in the water layer. The benzene used for the extraction was mixed with the first separated benzene layer.

The thus obtained benzene solution was dehydrated by adding 30 g of calcium chloride ($CaCl_2$) to the solution and allowing the mixture to stand overnight. The calcium chloride was then removed from the mixture by filtration. The resulting benzene solution was placed in a rotary evaporator and the benzene was then distilled away therefrom, whereby 13.5 g of a pale green solid residue was obtained. The yield was 65.9%. The melting point was 72.0° to 74.5° C.

The thus obtained residue was recrystallized from 200 ml of ethyl alcohol, so that 10.2 g of α-(p-dimethylaminophenyl)-α-(p-methylphenyl)ethylene was obtained as yellowish green crystals in the form of needles. The yield was 49.6%. The melting point was 76.5° to 77.5° C.

SYNTHESIS EXAMPLE 1-2

Synthesis of α-(p-dimethylaminophenyl)-α-(p-methoxyphenyl)ethylene

Synthesis Example 1-1 was repeated except that 20.7 g of 4-N,N-dimethylamino-4'-methylbenzophenone employed in Synthesis Example 1-1 was replaced by 22.1 g of 4-N,N-dimethylamino-4'-methoxybenzophenone, so that 15.9 g of α-(p-dimethylaminophenyl)-α-(p-methoxyphenyl)ethylene was obtained as pale blue crystals in the form of scales. The yield was 72.6%. The melting point was 129.0° to 130.2° C.

SYNTHESIS EXAMPLE 1-3

Synthesis of α-(p-dimethylaminophenyl)-α-(p-chlorophenyl)ethylene

Synthesis Example 1-1 was repeated except that 20.7 g of 4-N,N-dimethylamino-4'-methylbenzophenone employed in Synthesis Example 1-1 was replaced by 22.45 g of 4-N,N-dimethylamino-4'-chlorobenzophenone, so that 15.9 g of α-(p-dimethylaminophenyl)-α-(p-chlorophenyl)-ethylene was obtained as pale yellow crystals in the form of scales. The yield was 71.3%. The melting point was 116.5° to 117.0° C.

SYNTHESIS EXAMPLE 1-4

Synthesis of α-(p-dimethylaminophenyl)-α-phenylethylene

Synthesis Example 1-1 was repeated except that 20.7 g of 4-N,N-dimethylamino-4'-methylbenzophenone employed in Synthesis Example 1-1 was replaced by 19.5 g of 4-N,N-dimethylaminobenzophenone, so that 10.15 g of α-(p-dimethylaminophenyl)-α-phenylethylene was obtained as pale bluish green crystals in the form of needles. The yield was 52.6%. The melting point was 53.5° to 54.0° C.

SYNTHESIS EXAMPLE 1-5

Synthesis of α-(p-di-n-butylaminophenyl)-α-(p-methoxyphenyl-)ethylene

In a stream of nitrogen, 4.2 g of magnesium and 50 ml of absolute diethyl ether were placed in a 1-liter four-necked flask and stirred. To this mixture, a mixed solution of 25 g of methyl iodide and 50 ml of absolute diethyl ether was slowly added dropwise at room temperature over a period of 90 minutes. After the addition of the mixed solution, the reaction mixture was refluxed for 1 hour, so that a Grignard agent was prepared.

To the Grignard agent placed in the four-necked flask, 500 ml of a benzene solution of 29.35 g of 4-N,N-di-n-butylamino-4'-methoxybenzophenone having a melting point of 62.5° to 64.5° C. was added dropwise over a period of 90 minutes, with the temperature kept at 15° to 20° C. under ice cooling. After the dropwise addition of the benzene solution of 4-N,N-di-n-butylamino-4'-methoxybenzophenone, the reaction mixture was refluxed for 1 hour and then allowed to stand overnight.

This reaction mixture was slowly added to 500 ml of the ice-cooled aqueous solution containing 40.6 g of glacial acetic acid and 77.3 g of ammonium chloride. The mixture was stirred at room temperature for 2 hours and then allowed to stand for a while.

The reaction mixture separated into a benzene layer in which a reaction product was contained and a water layer. The benzene layer was separated from this reaction mixture, and the water layer was extracted with benzene to obtain the reaction product contained in the water layer. The benzene used for the extraction was mixed with the first separated benzene layer.

The thus obtained benzene solution was dehydrated by adding 30 g of calcium chloride ($CaCl_2$) to the solution and allowing the mixture to stand overnight. The calcium chloride was then removed from the mixture by filtration. The resulting benzene solution was placed in a rotary evaporator and the residue was obtained as a yellow viscous material. The residue was subjected to column chromatography, whereby 19.8 g of the product was obtained as a pale yellow viscous material The yield was 77.2%. The product was found to be α-(p-di-n-butylaminophenyl)-α-(p-methoxyphenyl)ethylene as the results of elemental analysis, and the characteristic absorption bands in the $^1$H-NMR spectrum and IR spectrum.

SYNTHESIS EXAMPLE 2-1

Synthesis of 1,5-bis(p-dimethylaminophenyl)-1,5-bis-(p-methylphenyl)-2,4-pentadiene-1-ol-perchlorate 23.7 g of α-(p-dimethylaminophenyl)-α-(p-methylphenyl)-ethylene prepared in SYNTHESIS EXAMPLE 1-1, 20 ml of triethyl orthoformate and 100 ml of acetic anhydride were placed in a 300-ml. Erlenmeyer flask and stirred. To this mixture, 7.18 g of a 70% aqueous solution of perchloric acid was slowly added dropwise. After the dropwise addition of perchloric acid, the mixture was refluxed for 90 minutes. Crystals having metallic luster separated from the reaction mixture under reflux, and crystals further separated under ice cooling. The thus separated crystals were filtered off, washed with water several times and dried. Thus 21.9 g of 1,5-bis(p-dimethylaminophenyl)-1,5-bis-(p-methylphenyl)-2,4-pentadiene-1-ol-perchlorate was obtained. The yield was 75%. The melting point of the product was 209° to 209.5° C.

SYNTHESIS EXAMPLE 2-2

Synthesis of 1,5-bis(p-dimethylaminophenyl)-1,5-bis-(p-methoxyphenyl)-2,4-pentadiene-1-ol-perchlorate 25.3 g of α-(p-dimethylaminophenyl)-α-(p-methoxyphenyl)ethylene prepared in Synthesis Example 1-2, 20 ml of triethyl orthoformate and 100 ml of acetic anhydride were placed in a 300-ml. Erlenmeyer flask and stirred. To this mixture, 7.18 g of a 70% aqueous solution of perchloric acid was slowly added dropwise. After the dropwise addition of perchloric acid, the mixture was refluxed for 90 minutes. Crystals having metallic luster separated from the reaction mixture under reflux, and crystals further separated under ice cooling. The thus separated crystals were filtered off, washed with water several times and dried. Thus 25.3 g of 1,5-bis(p-dimethylaminophenyl)-1,5-bis-(p-methoxyphenyl)-2,4-pentadiene-1-ol-perchlorate was obtained. The yield was 81.9%. The melting point of the product was 198.0° to 198.5° C.

SYNTHESIS EXAMPLE 2-3

Synthesis of 1,5-bis(p-dimethylaminophenyl)-1,5-bis-(p-chlorophenyl)-2,4-pentadiene-1-ol-perchlorate 25.8 g of α-(p-dimethylaminophenyl)-α-(p-chlorophenyl)-ethylene prepared in Synthesis Example 1-3, 20 ml of triethyl orthoformate and 100 ml of acetic anhydride were placed in a 300-ml. Erlenmeyer flask and stirred. To this mixture, 7.18 g of a 70% aqueous solution of perchloric acid was slowly added dropwise. After the dropwise addition of perchloric acid, the mixture was refluxed for 90 minutes. Crystals having metallic luster separated from the reaction mixture under reflux, and crystals further separated under ice cooling. The thus separated crystals were filtered off, washed with water several times and dried. Thus 19.3 g of 1,5-bis(p-dimethylaminophenyl)-1,5-bis-(p-chlorophenyl)-2,4-pentadiene- 1-ol-perchlorate was obtained. The yield was 61.8%. The melting point of the product was 202.5° to 203.0° C.

SYNTHESIS EXAMPLE 2-4

Synthesis of 1,5-bis(p-dimethylaminophenyl)-1,5-diphenyl-2,4-pentadiene-1-ol-perchlorate 22.3 g of α-(p-dimethylaminophenyl)-α-phenylethylene prepared in Synthesis Example 11 -4, 20 ml of triethyl orthoformate and 100 ml of acetic anhydride were placed in a 300-ml. Erlenmeyer flask and stirred. To this mixture, 7.18 g of a 70% aqueous solution of perchloric acid was slowly added dropwise. After the dropwise addition of perchloric acid, the mixture was refluxed for 90 minutes. Crystals having metallic luster separated from the reaction mixture under reflux and crystals further separated under ice cooling. The thus separated crystals were filtered off, washed with water several times and dried. Thus 14.3 g of 1,5-bis(p-dimethylaminophenyl)-1,5-diphenyl-2,4-pentadiene-1-ol-perchlorate was obtained. The yield was 51.4%. The melting point of the product was 178.5° to 180° C.

SYNTHESIS EXAMPLE 2-5

Synthesis of 1,5-bis(p-di-n-butylaminophenyl)-1,5-bis-(p-methoxyphenyl)-2,4-pentadiene-1-ol-perchlorate 33.75 g of α-(p-di-n-butylaminophenyl)-α-(p-methoxyphenyl)ethylene prepared in Synthesis Example 1-5, 20 ml of triethyl orthoformate and 100 ml of acetic anhydride were placed in a 300-ml. Erlenmeyer flask and stirred. To this mixture, 7.18 g of a 70% aqueous solution of perchloric acid was slowly added dropwise After the dropwise addition of perchloric acid, the mixture was refluxed for 90 minutes Crystals having metallic luster separated from the reaction mixture under reflux, and crystals further separated under ice cooling. The thus separated crystals were filtered off, washed with water several times and dried. Thus 29.14 g of 1,5-bis(p-di-n-butylaminophenyl)-1,5-bis-(p-methoxyphenyl)-2,4-pentadiene-1-ol-perchlorate was obtained. The yield was 74.2% . The melting point of the product was 175° to 176° C.

EXAMPLE 1-1

1,5-bis-(p-dimethylaminophenyl)-1,5-bis-(p-methoxyphenyl)-1,4-pentadiene-3-p-toluenesulfoamide (Leuco Dye No. 1)

1.2 g of a 60% sodium hydride was dispersed in 200 ml of well-dried N,N-dimethylformamide (DMF) in a 300-ml. Erlenmeyer flask. To this dispersion, 5.14 g of p-toluenesulfoamide was slowly added at room temperature and the mixture was stirred for 1 hour. To this mixture, 12.3 g of 1,5-bis-(p-dimethylaminophenyl)-1,5-bis-(p-methoxy-phenyl)-2,4-pentadiene-1-ol-perchlorate prepared in Synthesis Example 2-2 was slowly added. This reaction mixture was stirred at room temperature for 1 hour.

Then the reaction mixture was poured into 1 l of ice water. As a result, solids separated from the reaction mixture. The solids were washed with water and dried under reduced pressure. After the completion of drying, the solids were recrystallized from 100 ml of toluene, so that 9.18 g of the reaction product was obtained in the form of almost white crystals. The yield was 66.7%. The melting point of the product was 149.5° to 151.0° C.

The thus obtained crystals were further recrystallized from 70 ml of acetone, whereby 7.88 g of 1,5-bis-(p-dimethylaminophenyl)-1,5-bis-(p-methoxyphenyl)-1,4-pentadiene-3-p-toluenesulfoamide (Leuco Dye No. 1) according to the present invention was obtained in the form of white crystals. The yield was 57.3%. The melting point was 152.5° to 153.5° C. The characteristics absorption bands in the infrared spectrum of the thus obtained product were as follows:

Infrared light absorption spectrum (by KBr tablet): 3335 cm $cm^{-1}$, 2900 to 2960 $cm^{-1}$, 2850 $cm^{-1}$, 2810 $cm^{-1}$, 1610 $cm^{-1}$, 1520 $cm^{-1}$, 1360 $cm^{-1}$, 1330 $cm^{-1}$, 1250 $cm^{-1}$, 1160 $cm^{-1}$, 1035 $cm^{-1}$and 820 $cm^{-1}$.

EXAMPLE 1-2

1,5-bis-(p-dimethylaminophenyl)-1,5-bis-(p-methoxyphenyl)-1,4-pentadiene-3-α-naphthalenesulfoamide (Leuco Dye No. 4)

1.2 g of a 60% sodium hydride was dispersed in 200 ml of well-dried N,N-dimethylformamide (DMF) in a 300-ml. Erlenmeyer flask. To this dispersion, 6.22 g of α-naphthalenesulfoamide was slowly added at room temperature and the mixture was stirred for 1 hour. To this mixture, 12.3 g of 1,5-bis-(p-dimethylaminophenyl)-1,5-bis-(p-methoxyphenyl)-2,4-pentadiene-1-ol-perchlorate prepared in Synthesis Example 2—2 was slowly added. This reaction mixture was stirred at room temperature for 1 hour.

Then the reaction mixture was poured into 1 l of ice water. As a result, solids separated from the reaction mixture. The solids were washed with water and dried under reduced pressure. After the completion of drying, the solids were recrystallized from cyclohexane-toluene, so that 10.86 g of 1,5-bis-(p-dimethylaminophenyl)-1,5-bis-(p-methoxyphenyl-1)-1,4-pentadiene-3-α-naphthalenesulfoamide (Leuco Dye No. 4) according to the present invention was obtained in the form of almost white crystals. The yield was 75.0%. The melting point was 112.5° to 114.5° C. The characteristics absorption bands in the infrared spectrum of the thus obtained product were as follows:

Infrared light absorption spectrum (by KBr tablet): 2940 $cm^{-1}$, 2850 $cm^{-1}$, 2800 $cm^{-1}$, 1610 $cm^{-1}$, 1520 $cm^{-1}$, 1445 $cm^{-1}$, 1360 $cm^{-1}$, 1330 $cm^{-1}$, 1250 $cm^{-1}$, 1160 $cm^{-1}$, 1035 $cm^{-1}$ and 820 $cm^{-1}$.

EXAMPLE 1-3

1,5-bis-(p-dimethylaminophenyl)-1,5-bis-(p-methoxyphenyl)-1,4-pentadiene-3-β-naphthalenesulfoamide (Leuco Dye No. 5)

1.2 g of a 60% sodium hydride was dispersed in 200 ml of well-dried N,N-dimethylformamide (DMF) in a 300-ml. Erlenmeyer flask. To this dispersion, 6.22 g of β-naphthalenesulfoamide was slowly added at room temperature and the mixture was stirred for 1 hour. To this mixture, 12.3 g of 1,5-bis-(p-dimethylaminophenyl)-1,5-bis-(p-methoxyphenyl)-2,4-pentadiene-1-ol-perchlorate prepared in Synthesis Example 2—2 was slowly added. This reaction mixture was stirred at room temperature for 1 hour.

Then the reaction mixture was poured into 1 l of ice water. As a result, solids separated from the reaction mixture. The solids were washed with water and dried under reduced pressure After the completion of drying, the solids were recrystallized from cyclohexane-toluene, so that 10.50 g of the reaction product was obtained in the form of light reddish-brown crystals. The yield was 72.5%. The melting point of the product was 156° to 157° C.

The thus obtained crystals were further recrystallized from-acetone, whereby 7.20 g of 1,5-bis-(p-dimethylaminophenyl)-1,5-bis-(p-methoxyphenyl)-1,4-pentadiene-3-β-naphthalenesulfoamide (Leuco Dye No. 5) according to the present invention was obtained in the form of white crystals. The yield was 49.7%. The melting point was 163.8° to 164.5° C. The characteristics absorption bands in the infrared spectrum of the thus obtained product were as follows:

Infrared light absorption spectrum (by KBr tablet): 3260 $cm^{-1}$, 2900 to 2960 $cm^{-1}$, 2850 $cm^{-1}$, 2810 $cm^{-1}$, 1610 $cm^{-1}$, 1520 $cm^{-1}$, 1360 $cm^{-1}$, 1330 $cm^{-1}$, 1250 $cm^{-1}$, 1160 $cm^{-1}$, 1035 $cm^{-1}$ and 820 $cm^{-1}$.

EXAMPLE 1-4

1,5-bis-(p-dimethylaminophenyl)-1,5-bis-(p-methoxyphenyl)-1,4-pentadiene-3-p-methylbenzamide (Leuco Dye No. 7)

1.2 g of a 60% sodium hydride was dispersed in 200 ml of well-dried N,N-dimethylformamide (DMF) in a 300-ml. Erlenmeyer flask. To this dispersion, 4.06 g of p-methylbenzamide was slowly added at room temperature and the mixture was stirred for 1 hour. To this mixture, 12.3 g of 1,5-bis-(p-dimethylaminophenyl)-1,5-bis-(p-methoxyphenyl)-2,4-pentadiene-1-ol-perchlorate prepared in Synthesis Example 2-2 was slowly added. This reaction mixture was stirred at room temperature for 1 hour.

Then the reaction mixture was poured into 1 l of ice water. As a result, solids separated from the reaction mixture. The solids were washed with water and dried under reduced pressure. After the completion cf drying, the solids were recrystallized from cyclohexane, so that 10.4 g of 1,5-bis-(p-dimethylaminophenyl)-1,5-bis-(p-methoxy-phenyl)-1,4-pentadiene-3-p-methylbenzamide (Leuco Dye No. 7) according to the present invention was obtained in the form of light mud-yellow crystals. The yield was 79.8%. The melting point was 80° to 86.5° C. The characteristics absorption bands in the infrared spectrum of the thus obtained product were as follows:

Infrared light absorption spectrum (by KBr tablet): 3440 $cm^{-1}$, 2950 $cm^{-1}$, 2850 $cm^{-1}$, 2810 $cm^{-1}$, 1655 $cm^{-1}$, 1610 $cm^{-1}$, 1520 $cm^{-1}$, 1360 $cm^{-1}$, 1250 $cm^{-1}$, 1180 $cm^{-1}$, 1035 $cm^{-1}$ and 820 $cm^{-1}$.

EXAMPLE 1-5

1,5-bis-(p-dimethylaminophenyl)-1,5-bis-(p-methylphenyl)-1,4-pentadiene-3-malonic acid dimethyl ester (Leuco Dye No. 15)

1.2 g of a 60% sodium hydride was dispersed in 200 ml of well-dried N,N-dimethylformamide (DMF) in a 300-ml. Erlenmeyer flask. To this dispersion, 3.96 g of malonic acid dimethyl ester was slowly added at room temperature and the mixture was stirred for 1 hour. To this mixture, 11.7 g of 1,5-bis-(p-dimethylaminophenyl)-1,5-bis-(p-methylphenyl)-2,4-pentadiene-1-ol-perchlorate prepared in Synthesis Example 2-1 was slowly added. This reaction mixture was stirred at room temperature for 1 hour.

Then the reaction mixture was poured into 1 l of ice water. As a result, solids separated from the reaction mixture. The solids were washed with water and dried under reduced pressure. After the completion of drying, the solids were recrystallized from ethanol, so that 8.49 g of the reaction product was obtained in the form of almost white crystals. The yield was 68.8%. The melting point of the product was 159.5° to 163° C.

The thus obtained crystals were further recrystallized from acetone, whereby 7.34 g of 1,5-bis-(p-dimethylaminophenyl)-1,5-bis-(p-methylphenyl)-1,4-pentadiene-3-malonic acid dimethyl ester (Leuco Dye No. 15) according to the present invention was obtained in the form of white crystals. The yield was 59.5%. The melting point was 167.1° to 168.5° C. The characteristics absorption bands in the infrared spectrum of the thus obtained product were as follows:

Infrared light absorption spectrum (by KBr tablet): 3030 $cm^{-1}$, 3000 $cm^{-1}$, 2950 $cm^{-1}$, 2890 $cm^{-1}$, 2850 $cm^{-1}$, 2810 $cm^{-1}$, 1740 $cm^{-1}$, 1725 $cm^{-1}$, 1610 $cm^{-1}$, 1520 $cm^{-1}$, 1440 $cm^{-1}$, 1355 $cm^{-1}$, 1250 $cm^{-1}$, 1160 $cm^{-1}$, 1025 $cm^{-1}$, 950 $cm^{-1}$ and 820 $cm^{-1}$.

EXAMPLE 1-6

1,5-bis-(p-dimethylaminophenyl)-1,5-bis-(p-methoxylphenyl)-1,4-pentadiene-3-malonic acid dimethyl ester (Leuco Dye No. 16)

1.2 g of a 60% sodium hydride was dispersed in 200 ml of well-dried N,N-dimethylformamide (DMF) in a 300-ml. Erlenmeyer flask. To this dispersion, 3.96 g of malonic acid dimethyl ester was slowly added at room temperature and the mixture was stirred for 1 hour. To this mixture, 12.3 g of 1,5-bis-(p-dimethylaminophenyl)-1,5-bis-(p-methoxyl-phenyl)-2,4-pentadiene-1-ol-perchlorate prepared in Synthesis Example 2—2 was slowly added. This reaction mixture was stirred at room temperature for 1 hour.

Then the reaction mixture was poured into 1 l of ice water. As a result, solids separated from the reaction mixture. The solids were washed with water and dried under reduced pressure. After the completion of drying, the solids were recrystallized from ethanol, so that 9.72 g of the reaction product was obtained in the form of almost white crystals. The yield was 74.9%. The melting point of the product was 144° to 148.5° C.

The thus obtained crystals were further recrystallized from acetone, whereby 7.91 g of 1,5-bis-(p-dimethylaminophenyl)-1,5-bis-(p-methoxylphenyl)-1,4-pentadiene-3-malonic acid dimethyl ester (Leuco Dye No. 16) according to the present invention was obtained in the form of white crystals. The yield was 61.0%. The melting point was 152.5° to 153.5° C. The characteristics absorption bands in the infrared spectrum of the thus obtained product were as follows:

Infrared light absorption spectrum (by KBr tablet): 2960 $cm^{-1}$, 2900 $cm^{-1}$, 2850 $cm^{-1}$, 2810 $cm^{-1}$, 1760 $cm^{-1}$, 1735 $cm^{-1}$, 1610 $cm^{-1}$, 1520 $cm^{-1}$, 1450 $cm^{-1}$, 1360 $cm^{-1}$, 1250 $cm^{-1}$, 1175 $cm^{-1}$, 1035 $cm^{-1}$, 830 $cm^{-1}$ and 820 $cm^{-1}$.

EXAMPLE 1-7

1,5-bis-(p-dimethylaminophenyl)-1,5-bis-(phenyl)-1,4-pentadiene-3-malonic acid dimethyl ester (Leuco Dye No. 17)

1.2 g of a 60% sodium hydride was dispersed in 200 ml of well-dried N,N-dimethylformamide (DMF) in a 300-ml. Erlenmeyer flask. To this dispersion, 3.96 g of malonic acid dimethyl ester was slowly added at room temperature and the mixture was stirred for 1 hour. To this mixture, 11.14 g of 1,5-bis-(p-dimethylaminophenyl)-1,5-bis-(phenyl)-2,4- (-pentadiene-1-ol-perchlorate prepared in Synthesis Example 2-4 was slowly added. This reaction mixture was stirred at room temperature for 1 hour.

Then the reaction mixture was poured into 1 l of ice water. As a result, solids separated from the reaction mixture. The solids were washed with water and dried under reduced pressure. After the completion of drying, the solids were recrystallized from ethanol, so that 5.87 g of 1,5-bis-(p-dimethylaminophenyl)-1,5-bis-(phenyl)-1,4-pentadiene-3-malonic acid dimethyl ester (Leuco Dye No. 17) according to the present invention was obtained in the form of light orange crystals. The yield was 49.9%. The melting point was 77.5° to 82° C. The characteristics absorption bands in the infrared spectrum of the thus obtained product were as follows:

Infrared light absorption spectrum (by KBr tablet): 3040 $cm^{-1}$, 2960 $cm^{-1}$, 2900 $cm^{-1}$, 2850 $cm^{-1}$, 2810 $cm^{-1}$, 1740 $cm^{-1}$, 1610 $cm^{-1}$, 1520 $cm^{-1}$, 1445 $cm^{-1}$, 1355 $cm^{-1}$, 1160 $cm^{-1}$, 1035 $cm^{-1}$, 820 $cm^{-1}$ and 705 $cm^{-1}$.

EXAMPLE 1-8

1,5-bis-(p-dimethylaminophenyl)-1,5-bis-(p-chlorophenyl)-1,4-pentadiene-3-malonic acid dimethyl ester (Leuco Dye No. 18)

1.2 g of a 60% sodium hydride was dispersed in 200 ml of well-dried N,N-dimethylformamide (DMF) in a 300-ml. Erlenmeyer flask. To this dispersion, 3.96 g of malonic acid dimethyl ester was slowly added at room temperature and the mixture was stirred for 1 hour. To this mixture, 12.52 g of 1,5-bis-(p-dimethylaminophenyl)-1,5-bis-(p-chlorophenyl)-2,4-pentadiene-1-ol-perchlorate prepared in Synthesis Example 2-3 was slowly added. This reaction mixture was stirred at room temperature for 1 hour.

Then the reaction mixture was poured into 1 l of ice water. As a result, solids separated from the reaction mixture. The solids were washed with water and dried under reduced pressure. After the completion of drying, the solids were recrystallized from ethanol, so that 10.82 g of 1,5-bis-(p-dimethylaminophenyl)-1,5-bis-(p-chlorophenyl)-1,4-pentadiene-3-malonic acid dimethyl ester (Leuco Dye No. 18) according to the present invention was obtained in the form of almost white crystals. The yield was 82.3%. The melting point was 161.5° to 163.5° C. The characteristics absorption bands in the infrared spectrum of the thus obtained product were as follows:

Infrared light absorption spectrum (by KBr tablet): 3050 $cm^{-1}$, 3020 $cm^{-1}$, 2970 $cm^{-1}$, 2900 $cm^{-1}$, 2860 $cm^{-1}$, 2820 $cm^{-1}$, 1755 $cm^{-1}$, 1735 $cm^{-1}$, 1610 $cm^{-1}$, 1520 $cm^{-1}$, 1360 $cm^{-1}$, 1240 $cm^{-1}$, 1160 $cm^{-1}$, 1020 $cm^{-1}$ and 820 $cm^{-1}$.

EXAMPLE 1-9

1,5-bis-(p-dimethylaminophenyl)-1,5-bis-(p-methoxyphenyl)-1,4-pentadiene-3-malonitrile (Leuco Dye No. 19)

1.2 g of a 601 sodium hydride was dispersed in 200 ml of well-dried N,N-dimethylformamide (DMF) in a 300-ml. Erlenmeyer flask. To this dispersion, 1.98 g of malonitrile was slowly added at room. temperature and the mixture was stirred for 1 hour. To this mixture, 12.3 g of 1,5-bis-(p-dimethylaminophenyl)-1,5-bis-(p-methoxyphenyl)-2,4-pentadiene-1-ol-perchlorate prepared in Synthesis Example 2-2 was slowly added. This reaction mixture was stirred at room temperature for 1 hour.

Then the reaction mixture was poured into 1 of ice water. As a result, solids separated from the reaction mixture. The solids were washed with water and dried under reduced pressure. After the completion of drying, the solids were recrystallized from ethanol, so that 6.33 g of 1,5-bis-(p-dimethylaminophenyl)-1,5-bis-(p-methoxyphenyl)-1,4-pentadiene-3-malonitrile (Leuco Dye No. 19) according to the present invention was obtained in the form of light reddish brown crystals The yield was 54.3%. The melting point was 135° to 147.5° C. The characteristics absorption bands in the infrared spectrum of the thus obtained product were as follows:

Infrared light absorption spectrum (by KBr tablet): 2970 $cm^{-1}$, 2920 $cm^{-1}$, 2860 $cm^{-1}$, 2820 $cm^{-1}$, 2250 $cm^{-1}$, 1615 cm , 1520 $cm^{-1}$, 1450 $cm^{-1}$, 1360 $cm^{-1}$, 1250 $cm^{-1}$, 1180 $cm^{-1}$, 1040 $cm^{-1}$, 955 $cm^{-1}$ and 825 $cm^{-1}$.

EXAMPLE 1-10

1,5-bis-(p-dimethylaminophenyl)-1,5-bis-(p-methoxy-phenyl)-1,4-pentadiene-3-acetylacetone (Leuco Dye No. 20)

1.2 g of a 60% sodium hydride was dispersed in 200 ml of well-dried N,N-dimethylformamide (DMF) in a 300-ml. Erlenmeyer flask. To this dispersion, 3.00 g of acetylacetone was slowly added at room temperature and the mixture was stirred for 1 hour. To this mixture, 12.3 g of 1,5-bis-(p-dimethylaminophenyl)-1,5-bis-(p-methoxyphenyl)-2,4-pentadiene-1-ol-perchlorate prepared in Synthesis Example 2-2 was slowly added. This reaction mixture was stirred at room temperature for 1 hour.

Then the reaction mixture was poured into 1 l of ice water. As a result, solids separated from the reaction mixture. The solids were washed with water and dried under reduced pressure After the completion of drying, the solids were subjected to column chromatography and then recrystallized from n-hexane, so that 1,5-bis-(p-dimethylaminophenyl)-1,5-bis-(p-methoxyphenyl)-1,4-pentadiene-3-acetylacetone (Leuco Dye No. 20) according to the present invention was obtained in the form of white crystals. The melting point was 138° to 144° C. The characteristics absorption bands in the infrared spectrum of the thus obtained product were as follows:

Infrared light absorption spectrum (by KBr tablet): 3050 $cm^{-1}$, 3020 $cm^{-1}$, 2960 $cm^{-1}$, 2920 $cm^{-1}$, 2850 $cm^{-1}$, 2810 $cm^{-1}$, 1700 $cm^{-1}$, 1610 $cm^{-1}$, 1520 $cm^{-1}$, 1360 $cm^{-1}$, 1250 $cm^{-1}$, 1180 $cm^{-1}$, 1040 $cm^{-1}$ and 820 $cm^{-1}$.

EXAMPLE 1-11

1,5-bis-(p-dimethylaminophenyl)-1,5-bis-(p-methoxy-phenyl)-1,4-pentadiene-3-malonic acid diethyl ester (Leuco Dye No. 23)

1.2 g of a 60% sodium hydride was dispersed in 200 ml of well-dried N,N-dimethylformamide (DMF) in a 300-ml. Erlenmeyer flask. To this dispersion, 4.80 g of malonic acid diethyl ester was slowly added at room temperature and the mixture was stirred for 1 hour. To this mixture, 12.3 g of 1,5-bis-(p-dimethylaminophenyl)-1,5-bis-(p-methoxy-phenyl)-2,4-pentadiene-1-ol-perchlorate prepared in Synthesis Example 2-2 was slowly added. This reaction mixture was stirred at room temperature for 1 hour.

Then the reaction mixture was poured into 1 l of ice water. As a result, solids separated from the reaction mixture. The solids were washed with water and dried under reduced pressure. After the completion of drying, the solids were recrystallized from ethanol, so that 9.96 g of 1,5-bis-(p-dimethylaminophenyl)-1,5-bis-(p-methoxyphenyl)-1,4-pentadiene-3-malonic acid diethyl ester (Leuco Dye No. 23) according to the present invention was obtained in the form of almost white crystals. The yield was.73.6%. The melting point was 54.5° to 72.5° C. The characteristics absorption bands in the infrared spectrum of the thus obtained product were as follows:

Infrared light absorption spectrum (by KBr tablet): 3000 $cm^{-1}$, 2950 $c^{-1}$, 2910 $cm^{-1}$, 2850 $cm^{-1}$, 2810 $cm^{-1}$, 1760 $cm^{-1}$, 1735 $cm^{-1}$, 1610 $cm^{-1}$, 1520 $cm^{-1}$, 1360 $cm^{-1}$, 1250 $cm^{-1}$, 1180 $cm^{-1}$, 1160 $cm^{-1}$, 1040 $cm^{-1}$ and 825 $cm^{-1}$.

EXAMPLE 1-12

1,5-bis-(p-dimethylaminophenyl)-1,5-bis-(p-methoxy-phenyl)-1,4-pentadiene-3-malonic acid dibutyl ester (Leuco Dye No. 24)

1.2 g of a 60% sodium hydride was dispersed in 200 ml of well-dried N,N-dimethylformamide (DMF) in a 300-ml. Erlenmeyer flask To this dispersion, 6.49 g of malonic acid dibutyl ester was slowly added at room temperature and the mixture was stirred for 1 hour. To this mixture, 12.3 g of 1,5-bis-(p-dimethylaminophenyl)-1,5-bis-(p-methoxy-phenyl)-2,4-pentadiene-1-ol-perchlorate prepared in Synthesis Example 2-2 was slowly added. This reaction mixture was stirred at room temperature for 1 hour.

Then the reaction mixture was poured into 1 l of ice water. As a result, solids separated from the reaction mixture. The solids were washed with water-and dried under reduced pressure. After the completion of drying, the solids were recrystallized from ethanol, so that 10.14 g of 1,5-bis-(p-dimethylaminophenyl)-1,5-bis-(p-methoxyphenyl)-1,4-pentadiene-3-malonic acid dibutyl ester (Leuco Dye No. 24) according to the present invention was obtained in the form of white crystals. The yield was 69.2%. The melting point was 101.6° to 102.3° C. The characteristics absorption bands in the infrared spectrum of the thus obtained product were as follows:

Infrared light absorption spectrum (by KBr tablet): 2960 $cm^{-1}$, 2890 $cm^{-1}$, 2840 $cm^{-1}$, 2800 $cm^{-1}$, 1755 $cm^{-1}$, 1735 $cm^{-1}$, 1610 $cm^{-1}$, 1515 $cm^{-1}$, 1460 $cm^{-1}$, 1360 $cm^{-1}$, 1245 $cm^{-1}$, 1175 $cm^{-1}$, 1035 $cm^{-1}$, 950 $cm^{-1}$ and 825 $cm^{-1}$.

EXAMPLE 1-13

1,5-bis-(p-di-n-butylaminophenyl)-1,5-bis-(p-methoxy-phenyl)-1,4-pentadiene-3-acetylacetone (Leuco Dye No. 26)

1.2 g of a 60% sodium hydride was dispersed in 200 ml of well-dried N,N-dimethylformamide (DMF) in a 300-ml. Erlenmeyer flask. To this dispersion, 3.00 g of acetylacetone was slowly added at room temperature and the mixture was stirred for 1 hour. To this mixture, 15.71 g of 1,5-bis-(p-di-n-butylaminophenyl)-1,5-bis-(p-methoxyphenyl)-2,4-pentadiene-1-ol-perchlorate prepared in Synthesis Example 2,5 was slowly added. This reaction mixture was stirred at room temperature for 1 hour. Then the reaction mixture was poured into 1 l of ice water. As a result, solids separated from the reaction mixture. The solids were washed with water and dried under reduced pressure. After the completion of drying, the solids were subjected to column chromatography, so that 10.0 g of 1,5-bis-(p-di-n-butylaminophenyl)-1,5-bis-(p-methoxyphenyl)-1,4-pentadiene-3-acetylacetone (Leuco Dye No. 26 ) according to the present invention was obtained in the form of light yellow viscous material. The yield was 63.7%. The characteristics absorption bands in the infrared spectrum of the thus obtained product were as follows:

Infrared light absorption spectrum (by NaCl plate): 3040 $cm^{-1}$, 3010 $cm^{-1}$, 2960 $cm^{-1}$, 2940 $cm^{-1}$, 2880 $cm^{-1}$, 2850 $cm^{-1}$, 1700 $cm^{-1}$, 1610 $cm^{-1}$, 1520 $cm^{-1}$, 1465 $cm^{-1}$, 1370 $cm^{-1}$, 1250 $cm^{-1}$, 1180 $cm^{-1}$, 1040 $cm^{-1}$, 840 $cm^{-1}$, and 820 $cm^{-1}$.

EXAMPLE 1-14

11,5-bis-(p-di-n-butylaminophenyl)-1,5-bis-(p-methoxyphenyl)-1,4-pentadiene-3-malonic acid dimethyl ester (Leuco Dye No. 28)

1.2 g of a 60% sodium hydride was dispersed in 200 ml of well-dried N,N-dimethylformamide (DMF) in a 300-ml. Erlenmeyer flask. To this dispersion, 3.96 g of malonic acid dimethyl ester was slowly added at room temperature and the mixture was stirred for 1 hour. To this mixture, 15.71 g of 1,5-bis-(p-di-n-butylaminophenyl)-1,5-bis-(p-methoxy-phenyl)-2,4-pentadiene-1-ol-perchlorate prepared in Synthesis Example 2,5 was slowly added. This reaction mixture was stirred at room temperature for 1 hour.

Then the reaction mixture was poured into 1 l of ice water. As a result, solids separated from the reaction mixture. The solids were washed with water and dried under reduced pressure. After the completion of drying, the solids were subjected to column chromatography, so that 11.73 g of 1,5-bis-p-di-n-butylaminophenyl)-1,5-bis-(p-methoxyphenyl)-1,4-pentadiene-3-malonic acid dimethyl ester (Leuco Dye No. 28) according to the present invention was obtained in the form of light yellow viscous material. The yield was 71.8%. The characteristics absorption bands in the infrared spectrum of the thus obtained product were as follows:

Infrared light absorption spectrum (by NaCl plate): 3040 $cm^{-1}$, 3000 $cm^{-1}$, 2960 $cm^{-1}$, 2880 $cm^{-1}$, 2850 $cm^{-1}$, 2840 $cm^{-1}$, 1760 $cm^{-1}$, 1740 $cm^{-1}$, 1610 $cm^{-1}$, 1515 $cm^{-1}$, 1460 $cm^{-1}$, 1370 $cm^{-1}$, 1245 $cm^{-1}$, 1180 $cm^{-1}$, 1035 $cm^{-1}$, 835 $cm^{-1}$, and 815 $cm^{-1}$.

EXAMPLE 2-1

Preparation of Thermosensitive Recording Material No. 1

Liquid A-1, Liquid B-1, Liquid C-1 and Liquid D-1 were separately prepared by dispersing the following respective components in a ball mill:

| | Parts by Weight |
|---|---|
| (Liquid A-1) | |
| Leuco dye No. 16 prepared in Example 1-6 | 10 |
| 5% aqueous solution of methylcellulose | 20 |
| Water | 20 |
| (Liquid B-1) | |
| N-octadecyl(4-methoxycarbonyl) benzamide | 10 |
| 5% aqueous solution of methylcellulose | 20 |
| Water | 20 |
| (Liquid C-1) | |
| Calcium carbonate | 15 |
| 5% aqueous solution of methylcellulose | 15 |
| Water | 20 |
| (Liquid D-1) | |
| Bisphenol A | 10 |
| 10% aqueous solution of polyvinyl alcohol | 10 |
| Water | 30 |

Liquid A-1, Liquid B-1, Liquid C-1 and Liquid D-1 were mixed with a mixing ratio by weight of 1:2:3:3, so that a thermosensitive coloring layer coating liquid was prepared. The thus prepared thermosensitive coloring layer coating liquid was coated on a sheet of high quality paper having a basis weight of 50 g/ml, with a dye deposition amount of 0.40 g/ml on a dry basis, and then dried, whereby a thermosensitive recording material No. 1 according to the present invention was prepared.

The thus prepared thermosensitive recording material No. 1 was subjected to a printing test by use of a commercially available heat gradient test apparatus with application of heat at 130° C. for 1 second and a pressure of 2.0 $kg/cm^2$ to induce color formation in the recording material. The density of the induced colored images in the recording material and the background density thereof were measured by a Macbeth densitometer RD-514 equipped with a commercially available black film. The result was that the density of the induced color was 0.75 and the background density was 0.08. The induced color had a color tone of dark purple and the color induced area had a spectrum absorption in the range of about 400 to 950 nm, as shown in a curve 1 in the single FIGURE.

Further, the absorbance of the colored images and the absorbance of the background were measured by a commercially available spectrophotometer and then the thus measured values of absorbance were converted into the reflection ratios. The PCS (Printing Contrast Signal) value at 800 to 900 nm of the printed sample was obtained by the following formula:

$$PCS \text{ value } (\%) = \frac{\text{Reflection Ratio of Background} - \text{Reflection Ratio of Image Area}}{\text{Reflection Ratio of Background}} \times 100$$

As a result, the PCS value was 85% or more.

In addition, the thermosensitive recording material No. 1 was subjected to preservability tests under the following conditions:

1. stored at 60° C. in a dry state for 16 hours.
2. stored at 40° C. and a humidity of 90% for 16 hours.
3 stored in water for 16 hours.

As a result of the preservability tests, the decrease in the PCS value was hardly shown. Therefore, it was confirmed that the thermosensitive recording material No. 1 according to the present invention was capable of being read in the near infrared region more than 700 nm, and that it had excellent preservability.

EXAMPLE 2-2

Preparation of Thermosensitive Recording Material No. 2

The procedure of Example 2-1 was repeated except that Leuco Dye No. 16 employed in Liquid A in Example 2-1 was replaced by Leuco Dye No. 17 prepared in Example 1-7, whereby a thermosesitive recording material No. 2 according to the present invention was prepared.

The thus prepared thermosensitive recording material was subjected to the same printing test as in Example 2-1 so that the induced color, the image density and the background density were measured. The result was that the density of the induced color was 0.65 and the background density was 0.09. The induced color had a tone of dark brown and the color induced area had a sufficient spectrum absorption in the range of about 400 to 950 nm, as shown in a curve 2 in the single figure.

With respect to the PCS values before and after the preservability tests as employed in Example 2-1, the thermosensitive recording material No. 2 according to the present invention showed almost the same good results as in

EXAMPLE 2-1

EXAMPLE 2-3

Preparation of Thermosensitive Recording Material No. 3

The procedure of Example 2-1 was repeated except that Leuco Dye No. 16 employed in Liquid A in Example 2-1 was replaced by Leuco Dye No. 18 prepared in Example 1-8, whereby a thermosesitive recording material No. 3 according to the present invention was prepared.

The thus prepared thermosensitive recording material was subjected to the same printing test as in Example 2-1, so that the induced color, the image density and the background density were measured. The result was that the density of the induced color was 0.56 and the background density was 0.08. The induced color had a tone of dark reddish purple and the color induced area had a sufficient spectrum absorption in the range of about 400 to 950 nm, as shown in a curve 3 in the single FIGURE.

With respect to the PCS values before and after the preservability tests as employed in Example 2-1, the ) thermosensitive recording material No. 3 according to the present invention showed almost the same good results as in Example 2-1.

COMPARATIVE EXAMPLE 2-1

Preparation of Comparative Thermosensitive Recording Material No. 1

The procedure of Example 2-1 was repeated except that Leuco Dye No. 16 employed in Liquid A in Example 2-1 was replaced by a commercially available leuco dye (Trademark "PSD-150" made by Nippon Soda Co., Ltd.), whereby a comparative thermosesitive recording material No. 1 was prepared.

The thus prepared comparative thermosensitive recording material was subjected to the same printing test as in Example 2-1. The color induced hardly showed any absorption in the range of 700 nm or more, as shown in a curve 4 in the single FIGURE.

EXAMPLE 3-1

Preparation or Thermosensitive Recording Material No. 4

Liquid A-1 and Liquid B-1 were separately prepared by dispersing the following respective components in a ball mill:

| | |
|---|---|
| (Liquid A-1) | |
| Leuco dye No. 16 prepared in Example 1-6 | 20 g |
| 1% aqueous solution of polyvinyl alcohol | 80 g |
| (Liquid B-1) | |
| Bis-(3-aryl-4-hydroxyphenyl)-sulfone | 50 g |
| 1% aqueous solution of polyvinyl alcohol | 200 g |

Liquid A-1 and Liquid B-1 were mixed together. To this mixture, 250 g of 40%-dispersion of calcium carbonate, 40 g of 25%-dispersion of zinc stearate, 200 g of 25%-dispersion of stearic acid amide and then 625 g of 8% aqueous solution of polyvinyl alcohol were added with stirring, so that a thermosensitive coloring layer coating liquid was prepared. The thus prepared thermosensitive coloring layer coating liquid was coated on a sheet of paper having a basis weight of 55 g/ml, with a deposition of 6 g/ml on a dry basis, and then dried, whereby a thermosensitive recording material No. 4 was prepared.

EXAMPLE 3-2

Preparation of Thermosensitive Recording Material No. 5

The procedure of Example 3-1 was repeated except that bis-(3-aryl-4-hydroxyphenyl)sulfone employed in Liquid B-1 in Example 3-1 was replaced by bis-(4-hydroxyphenyl)sulfone, whereby a thermosensitive recording material No. 5 according to the present invention was prepared.

EXAMPLE 3-3

Preparation of Thermosensitive Recording Material No. 6

The procedure of Example 3-1 was repeated except that bis-(3-aryl-4-hydroxyphenyl)sulfone employed in Liquid B-1 in Example 3-1 was replaced by 2'-chlorobenzyl-3,4-hydroxybenzoate, whereby a thermosensitive recording material No. 6 according to the present invention was prepared.

EXAMPLE 3-4

Preparation of Thermosensitive Recording Material No. 7

The procedure of Example 3-1 was repeated except that bis-(3-aryl-4-hydroxyphenyl)sulfone employed in Liquid B-1 in Example 3-1 was replaced by 4'-ethylbenzyl-3,4-hydroxybenzoate, whereby a thermosensitive recording material No. 7 according to the present invention was prepared.

EXAMPLE 3-5

Preparation of Thermosensitive Recording Material No. 8

The procedure of Example 3-1 was repeated except that bis-(3-aryl-4-hydroxyphenyl)sulfone employed in Liquid B-1 in Example 3-1 was replaced by octadecyl gallate, whereby a thermosensitive recording material No. 8 according to the present invention was prepared.

EXAMPLE 3-6

Preparation of Thermosensitive Recording Material No. 9

The procedure of Example 3-1 was repeated except that bis-(3-aryl-4-hydroxyphenyl]sulfone employed in Liquid B-1 in Example 3-1 was replaced by 2-chlorobenzyl gallate, whereby a thermosensitive recording material No. 9 according to the present invention was prepared.

The thus prepared thermosensitive recording materials No. 4 to No. 9 according to the present invention were subjected to the following tests. The results are given in Table 2.

(1) Printing test

The thus prepared thermosensitive recording materials were subjected to the same printing test as in Example 2-1.

The density of the induced colored images in the recording materials and the background density thereof were measured by a Macbeth densitometer RD-918 equipped with a commercially available black film.

(2) Heat-resistance test

The thermosensitive recording materials with a developed colored image were stored at 60° C. for 24 hours. The heat resistance of the thermosensitive recording materials was assessed from the following formula:

$$\frac{\text{Colored image density after test}}{\text{Colored image density before test}} \times 100\%$$

(3) Water-resistance test

The thermosensitive recording materials with a developed colored image were dipped in 2 l of water of 20° C. for 20 -hours. The water resistance of the thermosensitive recording materials was assessed from the above formula in the same manner.

(4) Light-resistance test

The thermosensitive recording materials with a developed colored image were stored under an illuminance of 5000 lux for 100 hours. The light resistance of the thermosensitive recording materials was assessed from the above formula in the same manner.

The thermosensitive recording materials No. 4 and No. 5 were not subjected to the light-resistance test.

(5) Reading test by near infrared rays

The develoved colored images of the thermosensitive recording materials, in the form of bar-code, were subjected to a reading test by use of a commercially available GaAs semiconductor laser having a wavelength of 780 nm.

TABLE 2

| Item Exa. No. | Density of Colored Image | Heat-Resis-tance | Water-Resis-tance | Light-Resis-tance | Reading Test |
|---|---|---|---|---|---|
| 3-1 | 0.94 | 100% | 88% | — | possible |
| 3-2 | 0.85 | 100% | 84% | — | possible |
| 3-3 | 0.94 | 100% | 93% | 90% | possible |
| 3-4 | 1.03 | 100% | 88% | 91% | possible |
| 3-5 | 0.85 | 100% | 95% | 94% | possible |
| 3-6 | 0.91 | 100% | 93% | 92% | possible |

As previously mentioned, the thermosensitive recording materials comprising the leuco dyes having the above-mentioned formula (I) according to the present invention have the advantages that the induced colored images have a sufficient absorption intensity in the range of 400 to 950 nm, so that such colored images can be read by commercially available optical character readers, and other image readers using as a light source the light emitting diode and semiconductor laser, and that the manufacturing cost of the thermosensitive recording materials according to the present invention is low. In addition, the thermosensitive recording materials according to the present invention are capable of yielding image areas with a high image density, and heat-resistance, humidity-resistance, water-resistance and light-resistance are superior to other conventional recording materials.

Obviously, numerous (additional) modifications and variations of the present invention are possible in light of the above teachings. It is therefore to be understood that within the scope of the appended claims, the invention may be practiced otherwise than as specifically described herein.

What is claimed is:

1. A leuco dye of the formula (I):

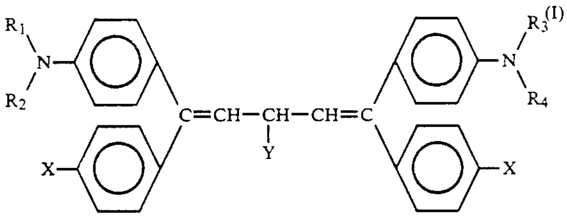
(I)

wherein $R_1$, $R_2$, $R_3$ and $R_4$ each represent an alkyl group having 1 to 10 carbon atoms; X represents hydrogen, an alkyl group having 1 to 10 carbon atoms, an alkoxyl group having 1 to 10 carbon atoms or a halogen; and Y represents $R_5$—Z—$SO_2NH$—, $R_6$—Z—CONH—, or

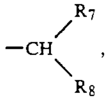
, in which Z represents

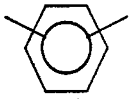 or 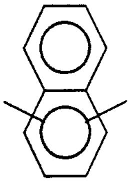 ;

$R_5$ and $R_6$ each represent hydrogen, an alkyl group having 1 to 10 carbon atoms, or a halogen; $R_7$ and $R_8$ each represent hydrogen, a cyano group, or —$COR_9$, in which $R_9$ represents a lower alkyl group, a lower alkoxyl group, or a phenyl group which may be substituted by an alkyl group having 1 to 4 carbon atoms, an alkoxyl group having 1 to 4 carbon atoms, or a halogen; or $R_9$ is a naphthyl group which may be substituted by an alkyl group having 1 to 4 carbon atoms, an alkoxyl group having 1 to 4 carbon atoms or halogen; with the proviso that $R_7$ and $R_8$ are not both hydrogen.

2. The leuco dye as claimed in claim 1, wherein $R_1$, $R_2$, $R_3$ and $R_4$ each represent an alkyl group selected from the group consisting of methyl group, ethyl group, propyl group, n-butyl group, iso-butyl group, pentyl group, hexyl group and heptyl group.

3. The leuco dye as claimed in claim 1, wherein $R_1$, $R_2$, $R_3$ and $R_4$ each represent an alkoxyl group selected from the group consisting of methoxy group, ethoxy group, propoxy group, n-butoxy group, iso-butoxy group and pentoxy group.

4. The leuco dye as claimed in claim 1, wherein X represents an alkyl group selected from the group consisting of methyl group, ethyl group, propyl group, n-butyl group, iso-butyl group, pentyl group, hexyl group and heptyl group.

5. The leuco dye as claimed in claim 1, wherein X represents an alkoxyl group selected from the group consisting of methoxy group, ethoxy group, propoxy group, n-butoxy group, iso-butoxy group and pentoxy group.

6. The leuco dye as claimed in claim 1, wherein X represents a halogen selected from the group consisting of chlorine, bromine and fluorine.

7. The leuco dye as claimed in claim 1, wherein Y represents $R_5$—Z—$SO_2NH$— in which $R_5$ represents hydrogen, an alkyl group having 1 to 10 carbon atoms, or a halogen, and Z represents

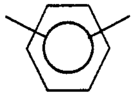 or 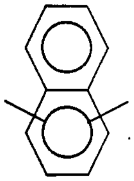 .

8. The leuco dye as claimed in claim 1, wherein Y represents $R_6$—Z—CONH— in which $R_6$ represents hydrogen, an alkyl group having 1 to 10 carbon atoms, or a halogen, and Z represents

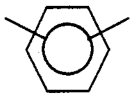 or 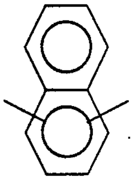 .

9. The leuco dye as claimed in claim 1, wherein Y represents

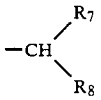

in which $R_7$ and $R_8$ each represent hydrogen, a cyano group, or —$COR_9$, in which $R_9$ represents a lower alkyl group, a lower alkoxyl group, a phenyl group which may be substituted by an alkyl group having 1 to 4 carbon atoms, an alkoxyl group having 1 to 4 carbon atoms, or a halogen; a naphthyl group which may be substituted by an alkyl group having 1 to 4 carbon atoms, an alkoxyl group having 1 to 4 carbon atoms or a halogen; with the proviso that $R_7$ $R_8$ are not both hydrogen.

* * * * *

UNITED STATES PATENT AND TRADEMARK OFFICE

CERTIFICATE OF CORRECTION

PATENT NO. : 5,084,593

DATED : January 28, 1992

INVENTOR(S) : H. Gotoh et al

It is certified that error appears in the above-identified patent and that said Letters Patent is hereby corrected as shown below:

Column 3, line 54, "a-thermosensitive" should read --a thermosensitive--.

Column 6, line 35, "hyiroxybenzamide" should read --hydroxybenzamide--.

Column 7, lines 5 and 6, "3-pchlorobenzenesulfonamide" should be --3-p-chlorobenzenesulfonamide--;
line 13, "dimethylaminophenvl" should read --dimethylaminophenyl--;
line 21, "1,5-bis(pmethyl-" should read --1,5-bis(p-methyl- --;
line 27, "1,5-bis(pmethoxy-" should read --1,5-bis(p-methoxy- --

Column 8, line 1, "1,5-bis(pmethyl-" should read --1,5-bis(p-methyl- --;
line 16, "1,5-bis(pmethoxy-" should read --1,5-bis(p-methoxy- --;
line 27, "1,5-bis(pmethoxy-" should read --1,5-bis(p-methoxy- --;
line 43, "1,5-brs" should read --1,5-bis--.

UNITED STATES PATENT AND TRADEMARK OFFICE
CERTIFICATE OF CORRECTION

PATENT NO. : 5,084,593

DATED : January 28, 1992

INVENTOR(S) : H. Gotoh et al

It is certified that error appears in the above-identified patent and that said Letters Patent is hereby corrected as shown below:

Column 15, line 30, "-1-alperchlorate" should read -- -1-al-perchlorate--.

Column 16, line 58, "4-(N-ethyl-N-ethoxypropyl)" should read --3-(N-ethyl-N-ethoxypropyl--; line 60, "tetrahyirofurfuryl" should read --tetrahydrofurfuryl--.

Column 19, line 23, "1 to 4 μm, when the prevention of" should read --0.1 to 5 μm, more--.

Column 23, line 3, "material" should read --material.--; lines 14-19, "23.7 g of α-(p-dimethylaminophenyl)-α-(p-methylphenyl)-ethylene prepared in Synthesis Example 1-1, 20 mℓ of triethyl orthoformate and 100 mℓ of acetic anhydride were placed in a 300-mℓ." should read as one sentence.

Column 24, line 13, "Synthesis Example 11-4" should read --Synthesis Example 1-4--.

Column 26, line 40, "methoxy-phenyl" should read --methoxyphenyl--.

Column 27, line 32, "(p-methoxy-phenyl)" should read --(p-methoxyphenyl)--.

Column 28, line 62, "601" should read --60%--.

UNITED STATES PATENT AND TRADEMARK OFFICE

CERTIFICATE OF CORRECTION

PATENT NO. : 5,084,593

DATED : January 28, 1992

INVENTOR(S) : H. Gotoh et la

It is certified that error appears in the above-identified patent and that said Letters Patent is hereby corrected as shown below:

Column 29, line 4, "1" should read --1ℓ--;
line 12, "crystals" should read --crystals.--;
line 67, "(p-methoxy-phenyl)" should read --(p-methoxyphenyl--.

Column 30, line 32, "(p-methoxy-phenyl)" should read --(p-methoxyphenyl)--.

Column 31, line 29, "(p-methoxy-phenyl)" should read --(p-methoxyphenyl)--;
line 39, "1,5-bis-p-di-n-buthylaminophenyl) should read --1,5-bis-(p-di-n-butylaminophenyl)--.

Column 32, line 24, "50 g/ml" should read --50 $g/m^2$--;
line 24, "0.40 g/ml" should read --0.40 $g/m^2$--.

Column 33, line 27, delete "EXAMPLE 2-1";
line 49, "the)" should read --the--.

UNITED STATES PATENT AND TRADEMARK OFFICE

CERTIFICATE OF CORRECTION

PATENT NO. : 5,084,593

DATED : January 28, 1992

INVENTOR(S) : H. Gotoh et al

It is certified that error appears in the above-indentified patent and that said Letters Patent is hereby corrected as shown below:

Column 34, line 31, "55 g/ml" should read --55 $g/m^2$--;
line 32, "6 g/ml" should read --6 $g/m^2$--.

Column 38, line 43, Claim 9, "$R_7$ $R_8$" should read --$R_7$ and $R_8$--.

Signed and Sealed this

Twenty-sixth Day of April, 1994

*Attest:*

BRUCE LEHMAN

*Attesting Officer*

*Commissioner of Patents and Trademarks*